US009380382B2

(12) United States Patent
Hopkins

(10) Patent No.: US 9,380,382 B2
(45) **Date of Patent: *Jun. 28, 2016**

(54) METHODS AND SYSTEMS FOR ACTIVE SOUND ATTENUATION IN A FAN UNIT

(71) Applicant: Nortek Air Solutions, LLC, Eden Prairie, MN (US)

(72) Inventor: Lawrence G. Hopkins, Happy Valley, OR (US)

(73) Assignee: Nortek Air Solutions, LLC, Saskatoon, Saskatchewan (CA)

( * ) Notice: Subject to any disclaimer, the term of this patent is extended or adjusted under 35 U.S.C. 154(b) by 748 days.

This patent is subject to a terminal disclaimer.

(21) Appl. No.: 13/626,423

(22) Filed: Sep. 25, 2012

(65) Prior Publication Data

US 2013/0022212 A1 Jan. 24, 2013

Related U.S. Application Data

(63) Continuation-in-part of application No. 13/044,695, filed on Mar. 10, 2011, now Pat. No. 9,091,280.

(60) Provisional application No. 61/324,634, filed on Apr. 15, 2010.

(51) Int. Cl.
*A61F 11/06* (2006.01)
*G10K 11/16* (2006.01)
(Continued)

(52) U.S. Cl.
CPC .............. *H04R 3/002* (2013.01); *F04D 29/663* (2013.01); *F04D 29/665* (2013.01); *F04D 29/667* (2013.01)

(58) Field of Classification Search
CPC ...... H04R 3/005; H04R 29/00; H04R 1/1083; H04R 2499/13; G10K 11/1788; G10K 11/178; G10K 2210/1282; G10K 11/1784; G10K 2210/1081; G10K 11/1786; G10K 2210/112; G10K 11/175
USPC ........... 381/71.3, 71.1, 71.2, 71.4, 71.5, 71.8, 381/56, 57
See application file for complete search history.

(56) References Cited

U.S. PATENT DOCUMENTS 4,508,486 A * 4/1985 Tinker .................. F04D 29/664 415/119
4,596,921 A 6/1986 Hersh
(Continued)

FOREIGN PATENT DOCUMENTS

CN 1180980 5/1998
CN 1333419 1/2002
(Continued)

OTHER PUBLICATIONS

International Search Report and Written Opinion for counterpart PCT/US2013/05530, mailed Nov. 27, 2013.
(Continued)

*Primary Examiner* — Paul S Kim
(74) *Attorney, Agent, or Firm* — Joseph M. Butscher; The Small Patent Law Group, LLC

(57) ABSTRACT

A system and method for controlling noise produced by an air handling system, for example, is provided. The system includes a source microphone to collect sound measurements from the air handling system and a processor to define a cancellation signal that at least partially cancels out the sound measurements. The system also includes a speaker to generate the cancellation signal. The sound measurements are at least partially canceled out within a region of cancellation. Accordingly, the system further includes a response microphone to collect response sound measurements at the region of cancellation. The processor tunes the cancellation signal based on the response sound measurements.

30 Claims, 16 Drawing Sheets

(51) Int. Cl.

| | |
|---|---|
| ***H03B 29/00*** | (2006.01) |
| ***H04R 3/00*** | (2006.01) |
| ***F04D 29/66*** | (2006.01) |

(56) References Cited

U.S. PATENT DOCUMENTS

| | | | | |
|---|---|---|---|---|
| 4,865,832 | A | 9/1989 | Kamijyo | |
| 4,965,832 | A | 10/1990 | Edwards | |
| 5,448,645 | A | 9/1995 | Guerci | |
| 5,511,127 | A | 4/1996 | Warnaka | |
| 5,515,444 | A | 5/1996 | Burdisso | |
| 5,832,095 | A | 11/1998 | Daniels | |
| 6,049,615 | A | 4/2000 | Chou | |
| 6,118,878 | A | 9/2000 | Jones | |
| 7,001,140 | B2 | 2/2006 | Hustvedt | |
| 7,317,801 | B1 | 1/2008 | Amir | |
| 7,357,621 | B2 | 4/2008 | Hustvedt | |
| 7,783,055 | B2 | 8/2010 | Barath | |
| 7,853,024 | B2 | 12/2010 | Slapak | |
| 7,869,607 | B2 | 1/2011 | Barath | |
| 2003/0112981 | A1 | 6/2003 | McWilliam | |
| 2004/0066940 | A1 | 4/2004 | Amir | |
| 2004/0194776 | A1 | 10/2004 | Amir | |
| 2005/0207585 | A1 | 9/2005 | Christoph | |
| 2008/0162072 | A1 | 7/2008 | Copley | |
| 2010/0002385 | A1 | 1/2010 | Lyon | |
| 2010/0002890 | A1 | 1/2010 | Lyon | |
| 2010/0014685 | A1 | 1/2010 | Wurm | |
| 2010/0028134 | A1* | 2/2010 | Slapak | F24F 13/24 415/119 |
| 2011/0116645 | A1 | 5/2011 | Slapak | |

FOREIGN PATENT DOCUMENTS

| | | |
|---|---|---|
| CN | 1755146 | 4/2006 |
| DE | 4421803 | 1/1996 |
| EP | 0619461 | 10/1994 |
| EP | 0 715 131 | 6/1996 |
| EP | 1 342 910 | 9/2003 |
| EP | 1342910 | 9/2003 |
| EP | 1357540 | 10/2003 |
| JP | 5-232968 | 9/1993 |
| JP | 5-289677 | 11/1993 |
| JP | 10-026384 | 1/1998 |
| JP | 10-143167 | 5/1998 |
| JP | 11-101492 | 4/1999 |
| JP | 2003-184799 | 7/2003 |
| JP | 2005 009377 | 1/2005 |
| JP | 2005 171838 | 6/2005 |
| JP | 2008-209098 | 9/2008 |
| KR | 1994-0004114 | 7/1993 |
| KR | 0111191 | 3/1996 |
| WO | WO 83-04287 | 12/1983 |
| WO | WO 2009/054429 | 4/2009 |

OTHER PUBLICATIONS

International Search Report and Written Opinion for counterpart PCT/US2011/027826, mailed Nov. 9, 2011.

"Implementation of Active Noise Control Into Different Fan Applications," Schneider, et al., Fan 2012, Apr. 2012.

"25 Years Ago, Active Control First Appeared as a Great Solution for Fan Noise. What Has Happened?" Wise, Fan 2012, Apr. 2012.

"Present and Future for Active Control of Fan Noise: Treatment At Source and in the Duct" Leventhall, et al., Fan Noise 2003, Sep. 2003.

The AcoustiFLO Modular Fan Model 686q Operation and Maintenance Manual.

International Preliminary Report on Patentability for counterpart application PCT/US2011/027826, issued Oct. 16, 2012.

Machine translation of JP2005171838.

* cited by examiner

METHODS AND SYSTEMS FOR ACTIVE SOUND ATTENUATION IN A FAN UNIT

CROSS REFERENCE TO RELATED APPLICATIONS

The present application is a continuation-in-part of U.S. patent application Ser. No. 13/044,695 filed Mar. 10, 2011, titled "Methods and Systems for Active Sound Attenuation in an Air Handling Unit." which, in turn, relates to and claims priority from U.S. Provisional Application Ser. No. 61/324, 634 filed Apr. 15, 2010, titled "Methods and Systems for Active Sound Attenuation in an Air Handling Unit" both of which are hereby expressly incorporated by reference in their entireties.

BACKGROUND OF THE INVENTION

Embodiments relate to air handling units and, more particularly, to methods and systems for active sound attenuation in a fan unit, which may be used in an air handling system, for example.

Air-handling systems (also referred to as air handlers) have traditionally been, used to condition buildings or rooms (hereinafter referred to as "structures"). An air-handling system may contain various components such as cooling coils, heating, coils, filters, humidifiers, fans, sound attenuators, controls, and other devices functioning to at least meet a specified air capacity which may represent all or only a portion of a total air handling requirement of the structure. The air-handling system may be manufactured in a factory and brought to the structure to be installed or it may be built on site using the appropriate devices to meet the specified air capacity. The air-handling compartment of the air-handling system includes the fan inlet cone and the discharge plenum. Within the air-handling compartment is situated the fan unit including an inlet cone, a fan, a motor, fan frame, and any appurtenance associated with the function of the fan (e.g. dampers, controls, settling means, and associated cabinetry). The fan includes a fan wheel having at least one blade. The fan wheel has as fan wheel diameter that is measured from one side of the outer periphery of the fan wheel to the opposite side of the outer periphery of the fan wheel. The dimensions of the air handling compartment such as height, width, and airway length are determined by consulting fan manufacturers data for the type of fan selected.

During operation, each fan unit produces sounds at many frequencies. In particular, smaller fan units typically emit sound at higher audible frequencies, whereas larger fan units emit more energy at lower audible frequencies. Devices have been proposed in the past that afford passive sound attenuation such as with acoustic absorption or sound barriers that block or reduce noise transmission. Acoustic absorption devices include a soft surface that converts sound energy to heat as the sound wave is reflected within the fan unit.

Some fan units are configured to control inlet noise through the use of sound traps located upstream of the fan. The sound traps may be located either in ductwork or in a special inlet section of an air handler enclosure. However, the sound traps typically occupy significant space in the ductwork or air handler enclosure. Moreover, the sound traps typically add significant cost to the fan units. Further, the sound traps typically do not provide for attenuation targeted at specific tonal nodes.

A need remains for improved systems and methods to provide sound attenuation in air handling systems.

SUMMARY OF THE INVENTION

In one embodiment, a method for controlling noise produced by an air handling system is provided. The method includes collecting sound measurements from the air handling system, wherein the sound measurements are defined by acoustic parameters. Values for the acoustic parameters are determined based on the sound measurements collected. Offset values for the acoustic parameters are calculated to define a cancellation signal that at least partially cancels out the fan noise and/or sound measurements when the cancellation signal is generated. The acoustic parameters may include a frequency and amplitude of the fan noise and/or sound measurements. Optionally, the cancellation signal includes an opposite phase and matching amplitude of the acoustic parameters. Optionally, response sound measurements are collected at a region of cancellation and the cancellation signal is tuned based on the response sound measurements.

In another embodiment, a system for controlling noise produced by an air handling system is provided. The system includes a source microphone to collect sound measurements from the air handling system and a processor to define a cancellation signal that at least partially cancels out the fan noise and/or sound measurements. The system also includes a speaker to generate the cancellation signal. Optionally, the speaker generates the cancellation signal in a direction opposite the sound measurements. Optionally, the fan noise and/or sound measurements are at least partially canceled out within a region of cancellation and the system further includes a response microphone to measure the sound field in, and/or collect response sound measurements at, the region of cancellation. Optionally, the processor tunes the cancellation signal based on the response sound measurements.

In another embodiment, a fan unit for an air handling system is provided. The fan unit includes a source microphone to collect sound measurements from the fan unit. A module defines a cancellation signal that at least partially cancels out the fan noise and/or sound measurements. A speaker generates the cancellation signal.

Certain embodiments provide a fan unit for an air handling system that may include a fan operatively connected to a motor and an inlet cone proximate to the fan. The inlet cone may include a noise control extension having a sound-absorbing layer configured to passively attenuate sound generated by the fan unit. The fan unit may also include a source microphone configured to collect sound measurements from the fan unit, and a speaker configured to generate a cancellation signal that at least partially cancels the fan noise and/or sound measurements.

The noise control extension may also include a perforated tube. The sound-absorbing layer may wrap around at least a portion of the perforated tube. The noise control extension further may also include a support tube that wraps around at least a portion of the sound-absorbing layer. The source microphone and the speaker may be secured to the support tube.

The inlet cone may include a throat proximate the fan, and a distal inlet. The noise control extension may extend between the throat and the distal inlet. The sound-absorbing layer of the noise control extension may be formed of a sound-absorbing material.

The noise control extension may be cylindrical. Optionally, the noise control extension may have a diameter that differs throughout a length of the noise control extension.

The fan unit may also include at least one response microphone configured to provide a feedback loop to a controller that feeds a cancellation signal to the speaker. Additionally, the fan unit may include a module configured to define the cancellation signal that at least partially cancels out the sound measurements.

Certain embodiments provide a method of attenuating noise within a fan unit for an air handling system. The fan unit may include a fan operatively connected to a motor and an inlet cone proximate to the fan. The method may include passively attenuating noise generated within the fan unit with a noise control extension having a sound-absorbing layer configured to passively attenuate sound generated by the fan. The method may also include actively attenuating noise generated within the fan unit. The actively attenuating noise operation may include collecting sound measurements from the fan unit through a source microphone, and generating a cancellation signal through a speaker.

The passively attenuating noise operation may also include supporting the sound-absorbing layer with a perforated tube, and allowing sound to pass into the sound-absorbing layer through the perforated tube. Also, the passively attenuating noise operation may include supporting the sound-absorbing layer with a support tube that wraps around at least a portion of the sound-absorbing layer.

The method may also include securing the source microphone and the speaker to the support tube. The method may also include disposing the noise control extension between a throat and distal end of the inlet cone. The method may also include forming the sound-absorbing layer from a sound-absorbing material. Additionally, the method may include using at least one response microphone to provide a feedback loop to the speaker. Also, the actively attenuating operation may include defining the cancellation signal within a module.

Certain embodiments provide a fan unit that may include a noise control extension having a sound-absorbing layer configured to passively attenuate sound generated by a fan unit, a source microphone configured to collect sound produced by the fan unit, and a speaker configured to generate a cancellation sound field that at least partially cancels the sound.

The noise control extension may also include a perforated tube. The sound-absorbing layer may wrap around at least a portion of the perforated tube. The noise control extension may also include a support tube that wraps around at least a portion of the sound-absorbing layer. The noise control extension may be configured to extend between a throat and a distal inlet of an inlet cone.

The source microphone and the speaker may be directly or indirectly secured to the support tube.

The sound-absorbing layer may be formed of an open-cell sound-absorbing material.

The noise control extension may be cylindrical. The noise control extension may include a diameter that differs throughout at least a portion of a length of the noise control extension.

The system may include at least one response microphone configured to provide a feedback loop to the speaker. The system may also include a module configured to define the cancellation signal that at least partially cancels out the sound measurements.

DETAILED DESCRIPTION OF THE DRAWINGS

Figure 1:
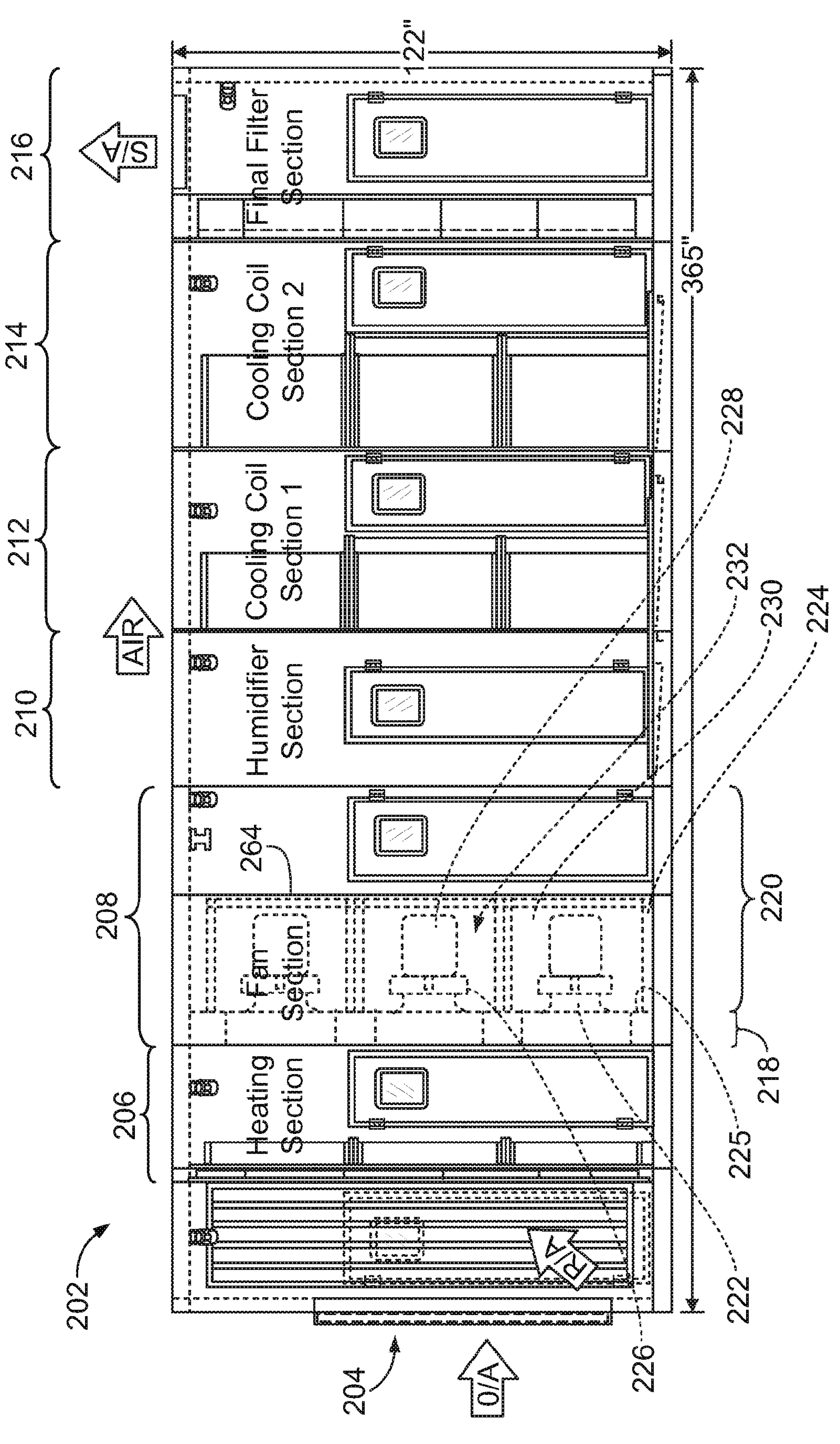
FIG. 1 is a perspective view of an air handler in accordance with an embodiment.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word “a” or “an” should be understood as not excluding plural of said elements or steps, unless such exclusion is explicitly stated. Furthermore, references to “one embodiment” are not intended to be interpreted as excluding the existence of additional embodiments that also incorporate the recited features. Moreover, unless explicitly stated to the contrary, embodiments “comprising” or “having" an element or a plurality of elements having a particular property may include additional such elements not having that property.

FIG. 1 illustrates an air handling system 202 that utilizes a fan array system in accordance with an embodiment of the present invention. The system 202 includes an inlet 204 that receives air. A heating section 206 that heats the air is included and followed by a fan section 208. A humidifier section 210 is located downstream of the fan section 208. The humidifier section 210 adds and/or removes moisture from the air. Cooling coil sections 212 and 214 are located downstream of the humidifier section 210 to cool the air. A filter section 216 is located downstream of the cooling coil section 214 to filter the air. The sections may be reordered or removed. Additional sections may be included.

The fan section 208 includes an inlet plenum 218 and a discharge plenum 220 that are separated from one another by a bulkhead wall 225 which forms part of a frame 224. Fan inlet cones 222 are located proximate to the bulkhead wall 225 of the frame 224 of the fan section 208. The fan inlet cones 222 may be mounted to the bulkhead wall 225. Alternatively, the frame 224 may support the fan inlet cones 222 in a suspended location proximate to, or separated from, the bulkhead wall 225. Fans 226 are mounted to drive shafts on individual corresponding motors 228. The motors 228 are mounted on mounting blocks to the frame 224. Each fan 226 and the corresponding motor 228 form one of the individual fan units 232 that may be held in separate chambers 230. The chambers 230 are shown vertically stacked upon one another in a column. Optionally, more or fewer chambers 230 may be provided in each column. One or more columns of chambers 230 may be provided adjacent one another in a single fan section 208.

Figure 2:
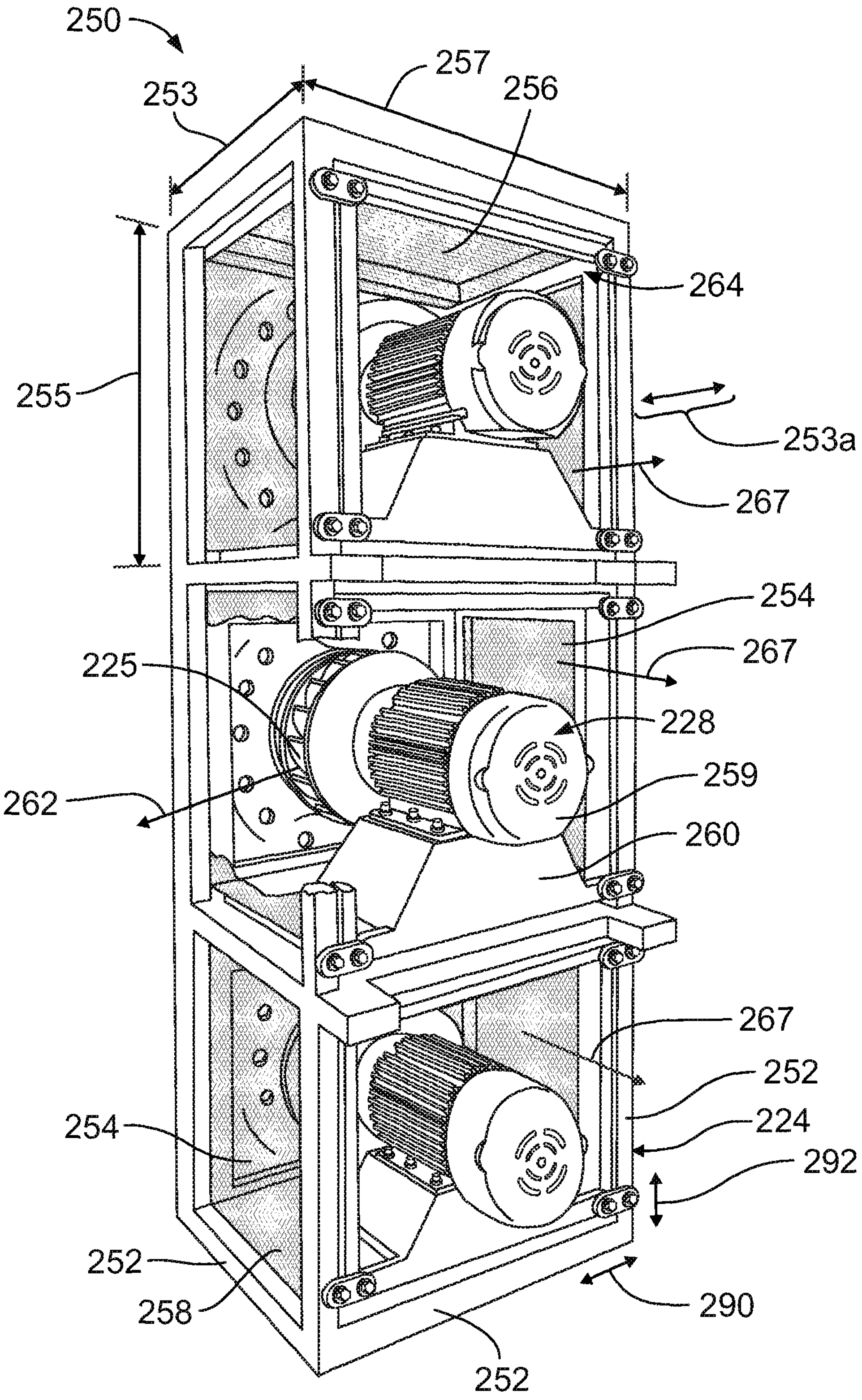
FIG. 2 is a perspective view of a stack of the fan arrays in accordance with an embodiment.

FIG. 2 illustrates a side perspective view of a column 250 of chambers 230 and corresponding fan units 232 therein. The frame 224 includes edge beams 252 extending horizontally and vertically along the top, bottom and sides of each chamber 230. Side panels 254 are provided on opposite sides of at least a portion of the fan unit 232. Top and bottom panels 256 and 258 are provided above and below at least a portion of the fan units 232. The top and bottom panels 256 may be provided above and below each fan unit 232. Alternatively, panels 256 may be provided above only the uppermost fan unit 232, and/or only below the lowermost fan unit 232. The motors are mounted on brackets 260 which are secured to the edge beams 252. The fans 226 are open sided plenum fans that draw air inward along the rotational axis of the fan and radially discharge the air about the rotational axis in the direction of arrow 262. The air then flows from the discharge end 264 of each chamber 230 in the direction of arrows 267.

The top, bottom and side panels 256, 258 and 254 have a height 255, a width 257 and a length 253 that are sized to form chambers 230 with predetermined volume and length. FIG. 2 illustrates the length 253 to substantially correspond to a length of the fan 226 and motor 228. Optionally, the length 253 of each chamber 230 may be longer than the length of the fan 226 and motor 228 such that the top, bottom and side panels 256, 258 and 254 extend beyond a downstream end 259 of the motors 228. For example, the panels 254, 256 and 258 may extend a distance, denoted by bracket 253*a*, beyond the downstream end 259 of the motor 228.

Figure 3:
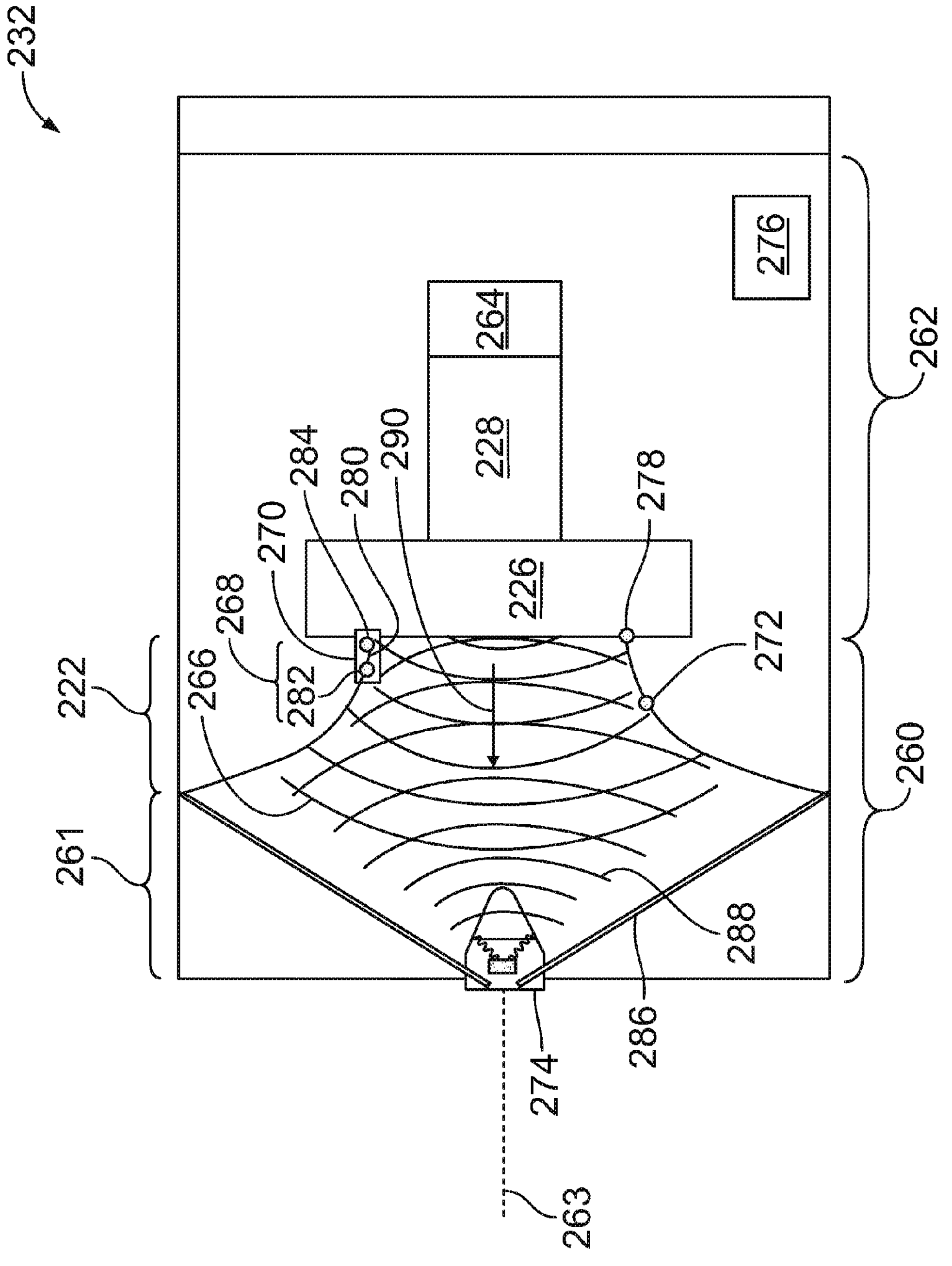
FIG. 3 is a schematic view of a fan unit in accordance with an embodiment.

FIG. 3 is a schematic view of an individual fan unit 232. The fan unit includes a fan 226 that is driven by a motor 228. An inlet cone 222 is coupled upstream of the fan 226 and includes a center axis 263. The fan unit 232 includes an upstream region 260 and a downstream region 262. A motor controller 264 is positioned adjacent the motor 228. Optionally, the motor controller 264 may be located adjacent one of top, bottom and side panels 256, 258 and 254, as shown in FIG. 2, and/or remote from the fan unit 232.

During operation, the motor 228 rotates the fan 226 to draw air through the inlet cone 222 from an inlet plenum 261 toward the downstream region 262. It should be noted that with respect to airflow, "upstream" is defined as traveling from the fan 226 to the inlet cone 222 and "downstream" is defined as traveling from the inlet cone 222 to the fan 226. The motor controller 264 may adjust a speed of the fan 226 to reduce or increase an amount of air flow through the fan unit 232. Noise may travel both upstream 260 and downstream 262 from the fan unit 232. The noise may include fan noise generated by vibrations or friction in the fan 226 or motor 228 among other things. The noise may also include environmental noise generated outside the fan unit 232. Both the fan noise and the environmental noise have acoustic parameters including frequency, wavelength, period, amplitude, intensity, speed, and direction. The noise travels in a noise vector 266.

The fan unit 232 includes active sound attenuation to reduce the fan noise within a region of active cancellation 268. The region of active cancellation 268 is in the throat 269 of the inlet cone 222. Optionally, the region of active cancellation 268 may be upstream from the inlet cone 222. In the exemplary embodiment, the region of active cancellation 268 is located in the upstream region 260. Optionally, the region of active cancellation 268 may be located in the downstream region 262. The active sound attenuation may reduce any one of the acoustic parameters to approximately zero using destructive interference. Destructive interference is achieved by the superposition of a sound waveform onto a original sound waveform to eliminate the original sound waveform by reducing or eliminating one of the acoustic parameters of the original waveform. In an exemplary embodiment, the amplitude of the noise vector 266 is reduced or substantially eliminated. Optionally, any of the acoustic parameters of the noise vector 266 may be eliminated.

Active sound attenuation is enabled by a source microphone 270, a response microphone 272, a speaker 274, and an attenuation module 276. The source microphone 270 is positioned within the inlet cone 222. The source microphone 270 is configured to detect the noise vector 266. The step of detecting the noise vector 266 includes obtaining sound measurements having acoustic parameters. For example, a sound pressure of the noise vector 266 may be obtained to determine the acoustic parameters. The source microphone 270 may be positioned at the juncture 278 of the inlet cone 222 and the fan 226. Optionally, the source microphone 270 may be positioned along any portion of inlet cone 222 or upstream from the inlet cone 222. In the exemplary embodiment, the source microphone 270 is located flush with an inner surface 280 of the inlet cone 222 to reduce disturbances in air flow through the inlet cone 222. Optionally, the source microphone 270 may extend toward the center axis 263 on a boom or bracket.

In the exemplary embodiment, the source microphone 270 includes a pair of microphones configured to bias against environmental noise. Optionally, the source microphone may only include one microphone. The pair of microphones includes a downstream microphone 282 and an upstream microphone 284. Optionally, source microphone 270 may include a plurality of microphones configured to bias against environmental noise. In one embodiment, the upstream microphone 284 may be positioned approximately 50 mm from the downstream microphone 282. Optionally, microphones 282 and 284 may have any suitable spacing. Further, in the exemplary embodiment, microphone 282 is positioned in approximately the same circumferential location as microphone 284. Optionally, microphones 282 and 284 may be positioned within different circumferential locations of the inlet cone 222.

Microphones 282 and 284 bias against environmental noise so that only fan noise is attenuated. Environmental noise is detected by the upstream microphone 284 and the downstream microphone 282 at substantially the same time. However, a time delay exists between downstream microphone 282 sensing the fan noise and upstream microphone 284 sensing the fan noise. Accordingly, the fan noise can be distinguished from the environmental noise and the environmental noise is removable from the noise vector 266.

The speaker 274 is positioned upstream from the inlet cone 222. The speaker 274 may be fabricated from a perforated foam or metal. For example, the speaker 274 may be fabricated from acoustically transparent foam. In an embodiment, the speaker 274 has an aerodynamic shape that has a limited effect on the fan performance. For example, the speaker 274 may be domed-shaped. In the exemplary embodiment, the speaker 274 is mounted on a tripod or similar mount 286. Optionally, the speaker 274 may be coupled to one of panels 254, 256 and 258 or to frame 224. Additionally, the speaker 274 may be positioned upstream of the fan unit and configured to attenuate noise within the entire fan unit. The speaker 274 is aligned with the center axis 263 of the inlet cone 222. Optionally, the speaker 274 may be offset from the center axis 263. The speaker 274 may also be angled toward the center axis 263. The speaker 274 transmits an attenuation signal 288 downstream and opposite the noise vector 266. The attenuation signal 288 is an inverted noise vector 266 having an opposite phase and matching amplitude of the noise vector 266. The attenuation signal 288 destructively interferes with the noise vector 266 to generate an attenuated noise vector 290 having an amplitude of approximately zero. Optionally, the attenuating vector 288 reduces any of the noise vector acoustic parameters so that the attenuated noise vector 290 is inaudible.

The response microphone 272 is positioned upstream of the source microphone 270 and within the region of active cancellation 268. The response microphone 272 is located flush along the inner surface 280 of the inlet cone 222. Optionally, the response microphone 272 may extend toward the center axis 263 on a boom or bracket. Additionally, the response microphone 272 may be positioned in the inlet plenum 261 and/or upstream of the fan unit. The response microphone 272 is configured to detect the attenuated noise vector 266. Detecting the attenuated noise vector 290 includes obtaining sound measurements having acoustic parameters. For example, a sound pressure of the attenuated noise vector 290 may be obtained to determine the acoustic parameters. As described in more detail below, the attenuated noise vector 290 is compared to the noise vector 266 to determine whether the noise vector 266 has been reduced or eliminated.

Typically, the noise vector 266 remains dynamic throughout the operation of the fan unit 232. Accordingly, the attenuation signal 288 must be modified to adapt to changes in the noise vector 266. The attenuating module 276 is positioned within the fan unit 232 to modify the attenuation signal 288. Optionally, the attenuating module 276 may be positioned within the air processing system 200 or may be remote therefrom. The attenuating module 276 may be programmed internally or configured to operate software stored on a computer readable medium.

Figure 4:
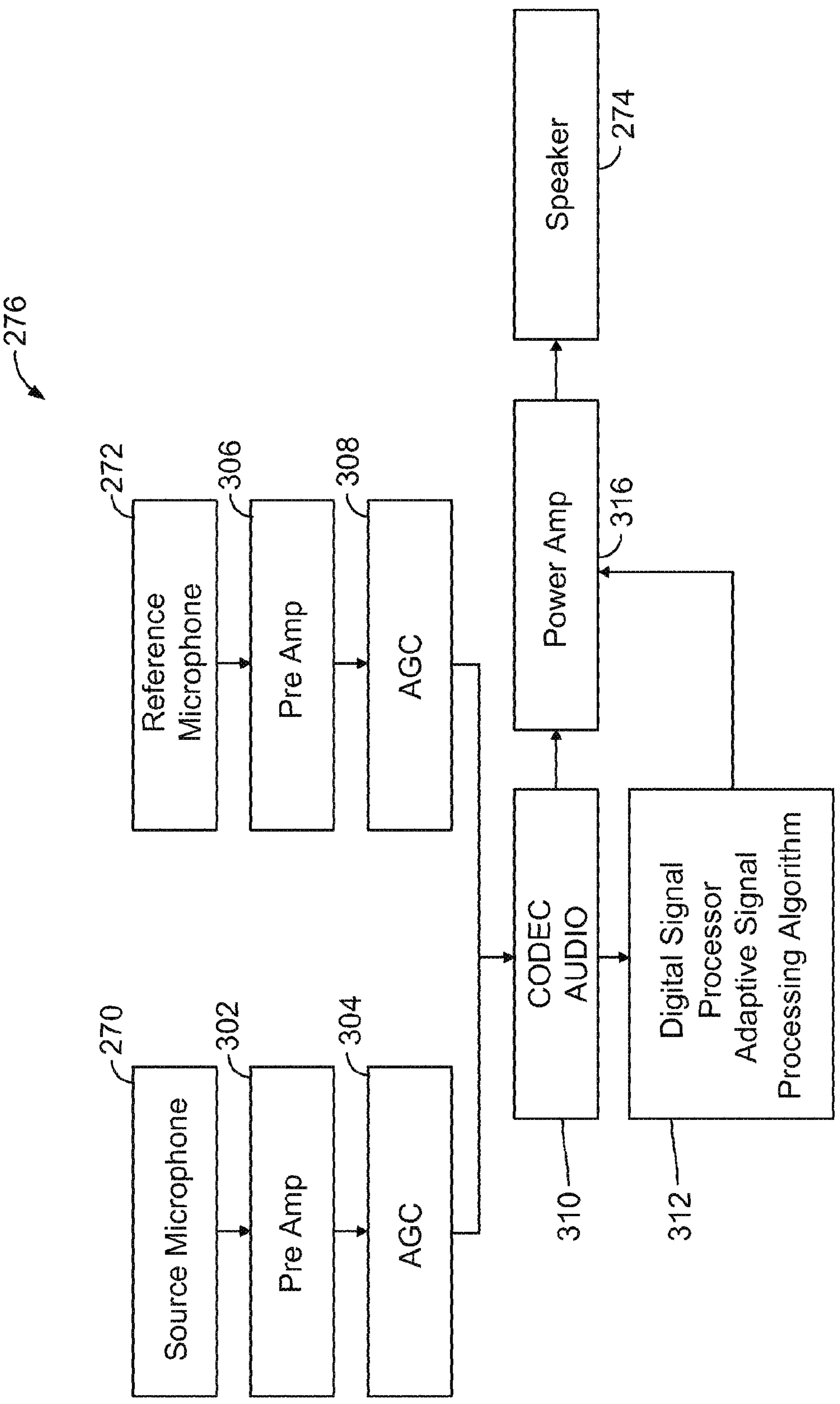
FIG. 4 is a flowchart of a method for a dynamic feedback loop in accordance with an embodiment.

FIG. 4 is a block diagram of the attenuating module 276 electronically coupled to an input microphone, such as the source microphone 270 and an error microphone, such as the response microphone 272. The attenuating module 276 includes a pre-amplifier 302 and an automatic gain control 304 to modify the noise vector 266 detected by the source microphone 270. Likewise, a pre-amplifier 306 and an automatic gain control 308 modify the attenuated noise vector 290 detected by the response microphone 272. A CODEC 310 digitally encodes the noise vector 266 and the attenuated noise vector 290. A digital signal processor 312 obtains the acoustic parameters of each vector 266 and 290. The digital signal processor 312 may compare the vectors may by utilizing an adaptive signal processing algorithm to determine whether the noise vector 266 has been attenuated. Based on the comparison, the attenuation module 276 modifies the attenuation signal 288, which is digitally decoded by the CODEC 310, transmitted to an amplifier 316, and output by the speaker 274.

Figure 5:
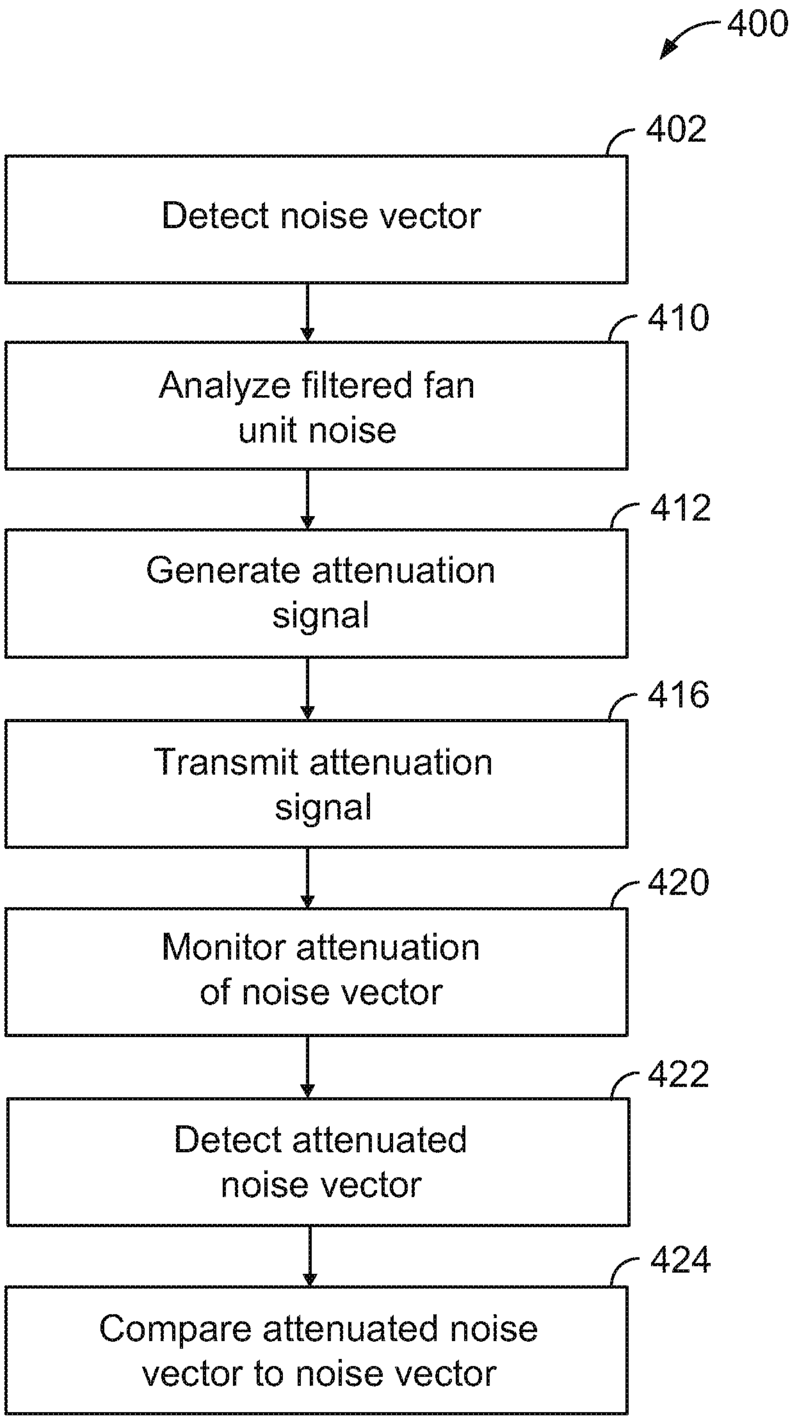
FIG. 5 is a flowchart of a method for providing active sound attenuation in accordance with an embodiment.
Figure 6:
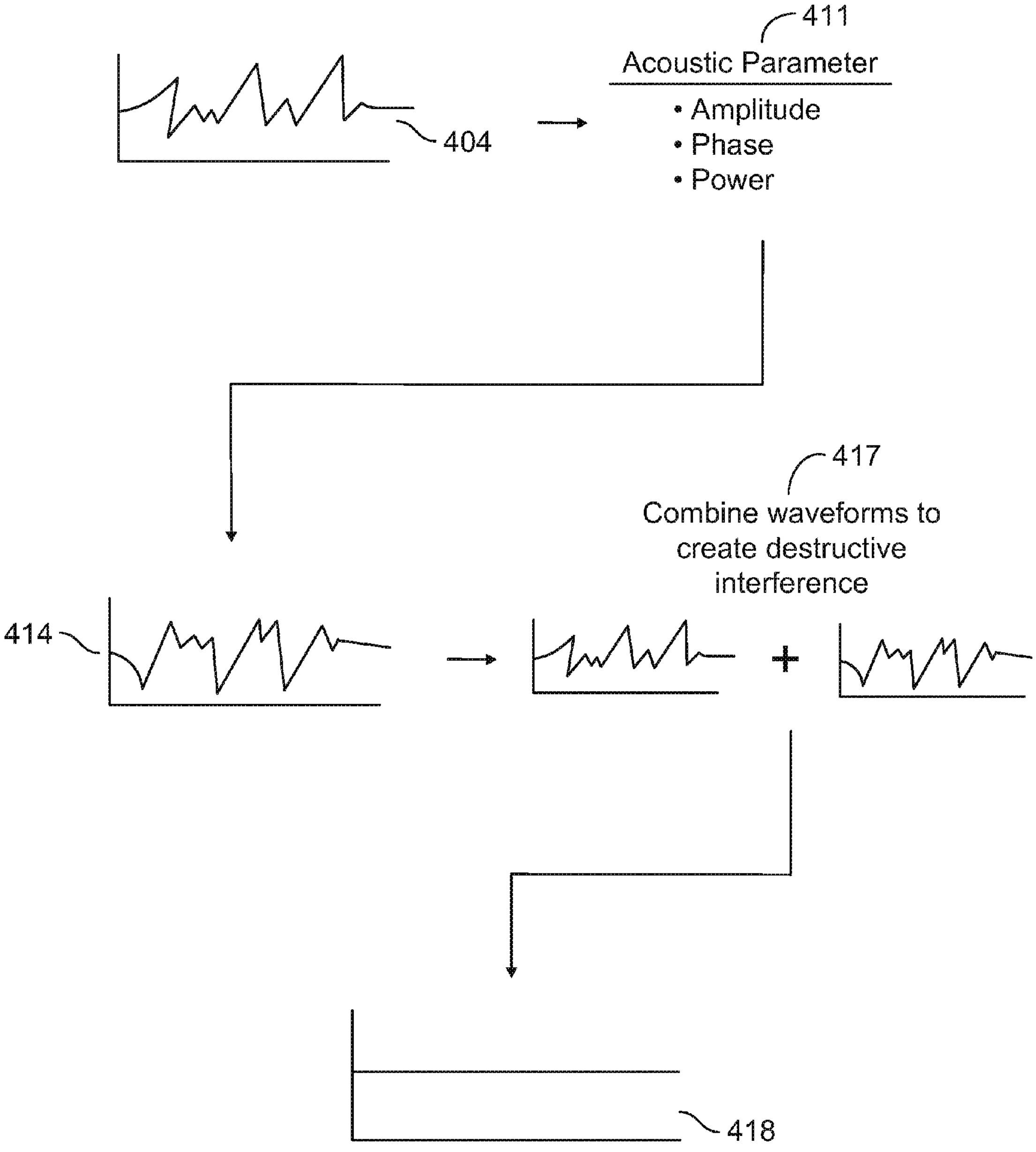
FIG. 6 is a pictorial graphic corresponding to the active sound attenuation method of FIG. 5.

FIG. 5 illustrates a method 400 for active attenuation of the noise vector 266. FIG. 6 is a pictorial graphic corresponding to active attenuation. During operation of the fan unit 232 the noise vector 266 travels from the fan unit 232. Optionally, the noise may be a scalar value. For example, the noise may merely be a value representing a magnitude of noise. At 402, the source microphone 270 detects the noise vector 266. Detecting the noise vector 266 may include detecting a sound pressure, intensity and/or frequency of the noise vector 266. The noise vector is detected as a waveform 404, as shown in FIG. 6.

At 410, the filtered fan unit noise is analyzed to obtain values for the acoustic parameters 411 of the sound measurements. The acoustic parameters 411 may be calculated using an algorithm, determined using a look-up table, and/or may be pre-determined and stored in the attenuation module 276. The acoustic parameters of interest may include the frequency, wavelength, period, amplitude, intensity, speed, and/or direction of the filtered fan unit noise. At 412, an attenuation signal 414 is generated. The attenuation signal 414 may be generated by inverting the waveform of the filtered fan unit noise 408. As shown in FIG. 6, the attenuation signal 414 has an equal amplitude and a waveform that is 180 degrees out of phase with the filtered fan unit noise waveform 408.

At 416, the attenuation signal 414 is transmitted to the speaker 274 to generate the attenuation signal 288. The attenuation signal 288 is transmitted downstream in a direction opposite the noise vector 266. The attenuation signal 288 has a matching amplitude and opposite phase in relation to the noise vector 266. Thus, the attenuation signal 288 destructively interferes 417 with the noise vector 266 by reducing the amplitude of the noise vector 266 to approximately zero, as shown at 418 of FIG. 6. It should be noted that the amplitude may be reduced to any range that is inaudible. Optionally, the attenuation signal 288 may reduce or eliminate any other acoustic parameter of the noise vector 266. Further, in the exemplary embodiment, the attenuation signal 288 is timed so that the noise vector 266 is attenuated within the region of active cancellation 268, thereby also eliminating the noise vector 266 upstream of the region of active cancellation 268.

At 420, the response microphone 272 monitors attenuation of the noise vector 266. In the exemplary embodiment, the response microphone 272 monitors the attenuation in real-time. As used herein real-time refers to actively monitoring the attenuation as the attenuation signal 288 is transmitted from the speaker 274.

At 422, the response microphone 272 detects the attenuated noise vector 290. At 424, the attenuated noise vector 290 is compared to the noise vector 266 to provide a dynamic feedback loop that adjusts and tunes the attenuation signal 288.

Figure 7:
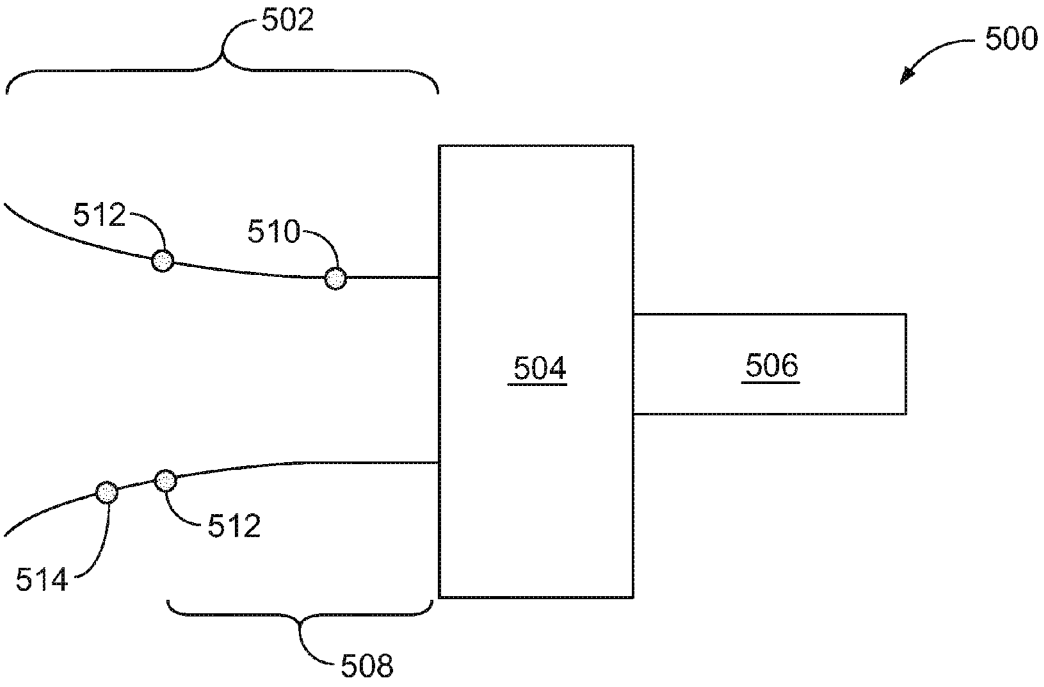
FIG. 7 is a schematic view of a fan unit in accordance with an embodiment.

FIG. 7 illustrates a fan unit 500 in accordance with an embodiment. The fan unit 500 includes an inlet cone 502, a fan 504, and a motor 506. The inlet cone 502 is positioned upstream from the fan 504. The inlet cone 502 includes a throat 508 positioned directly upstream from the fan 504. It should be noted that with respect to airflow "upstream" is defined as traveling from the fan 504 to the inlet cone 502 and "downstream" is defined as traveling from the inlet cone 502 to the fan 504. A source microphone 510 is positioned within the throat 508 of the inlet cone 502. The source microphone 510 may include two or more microphones. Optionally, the source microphone 510 may include only one microphone. A pair of speakers 512 is positioned upstream from the source microphone 510. Optionally, there may more or less speakers 512 than shown. The speakers 512 are positioned within the inlet cone 502. In an embodiment, the speakers 512 are positioned within the same cross-sectional plane. Optionally, the speakers 512 may be offset from one another. A response microphone 514 is positioned upstream of the speakers 512. The response microphone 514 is positioned within the inlet cone 502. Optionally, the response microphone 514 may be positioned upstream of the fan unit 500.

Noise generated by the fan 504 travels upstream. The noise is detected by the source microphone 510. In response to the detected noise, the speakers 512 transmit attenuating sound fields configured to destructively interfere with the noise. The result of the destructive interference is detected by the response microphone 514 to provide a feedback loop to the speakers 512.

Figure 8:
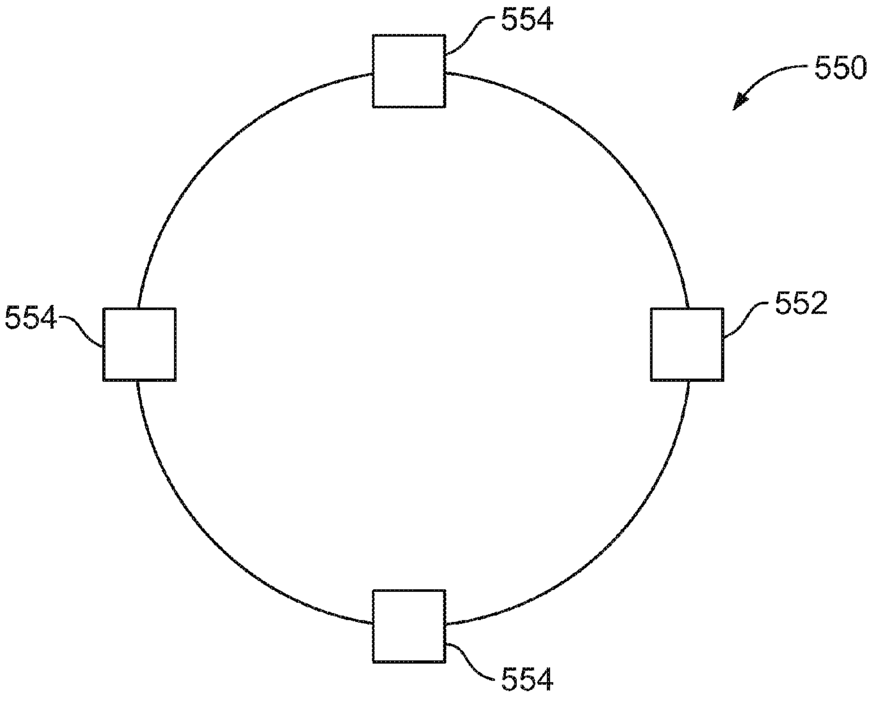
FIG. 8 is a cross-sectional view of an inlet cone in accordance with an embodiment.

FIG. 8 illustrates a cross-section of an inlet cone 550 in accordance with an embodiment. The inlet cone 550 includes a source microphone 552 and speakers 554. The source microphone 552 and the speakers 554 are each positioned 90 degrees from each other. Optionally, the source microphone 552 and the speakers 554 may be positioned along any portion of the inlet cone circumference. Additionally, the inlet cone 550 may include a pair of source microphones 552 and/or any number of speakers 554. In the example embodiment, the source microphone 552 and the speakers 554 are each positioned in the same cross-sectional plane of the inlet cone 550. Optionally, the source microphone 552 and the speakers 554 may be offset from one another.

Noise travels along the inlet cone 550. The noise is detected by the source microphone 552. The speakers then generate an attenuation sound field to destructively interfere with the noise.

Figure 9:
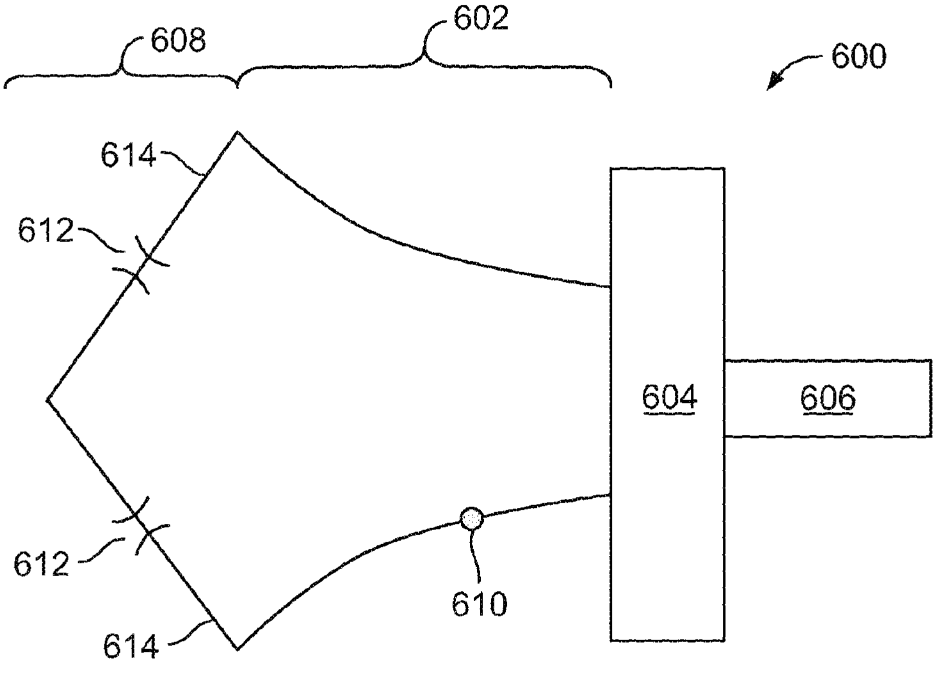
FIG. 9 is a schematic view of a fan unit in accordance with an embodiment.

FIG. 9 illustrates a fan unit 600 in accordance with an embodiment. The fan unit 600 includes an inlet cone 602, a fan assembly 604, and a motor 606. The inlet cone 602 is positioned upstream from the fan assembly 604. An inlet plenum 608 is positioned upstream from the inlet cone 602. It should be noted that with respect to airflow "upstream" is defined as traveling from the fan 604 to the inlet cone 602 and "downstream" is defined as traveling from the inlet cone 602 to the fan 604. A source microphone 610 is positioned within the inlet cone 602. The source microphone 610 may include a pair of microphones. Optionally, the source microphone 610 may include only one microphone. A pair of speakers 612 is positioned within the inlet plenum 608. Optionally, fan unit 600 may include any number of speakers 612. The speakers 612 are aerodynamically configured to limit an effect on the fan performance. The speakers 612 are coupled to a strut 614 that extends through the inlet plenum 608 and across an opening of the inlet cone 602. The strut 614 is angled to angle the speakers 612 with respect to one another. Optionally, the strut may be arced and configured to retain any number of speakers 612.

Noise generated by the fan 604 travels upstream. The noise is detected by the source microphone 610. In response to the detected noise, the speakers 612 transmit attenuating sound fields configured to destructively interfere with the noise.

Figure 10:
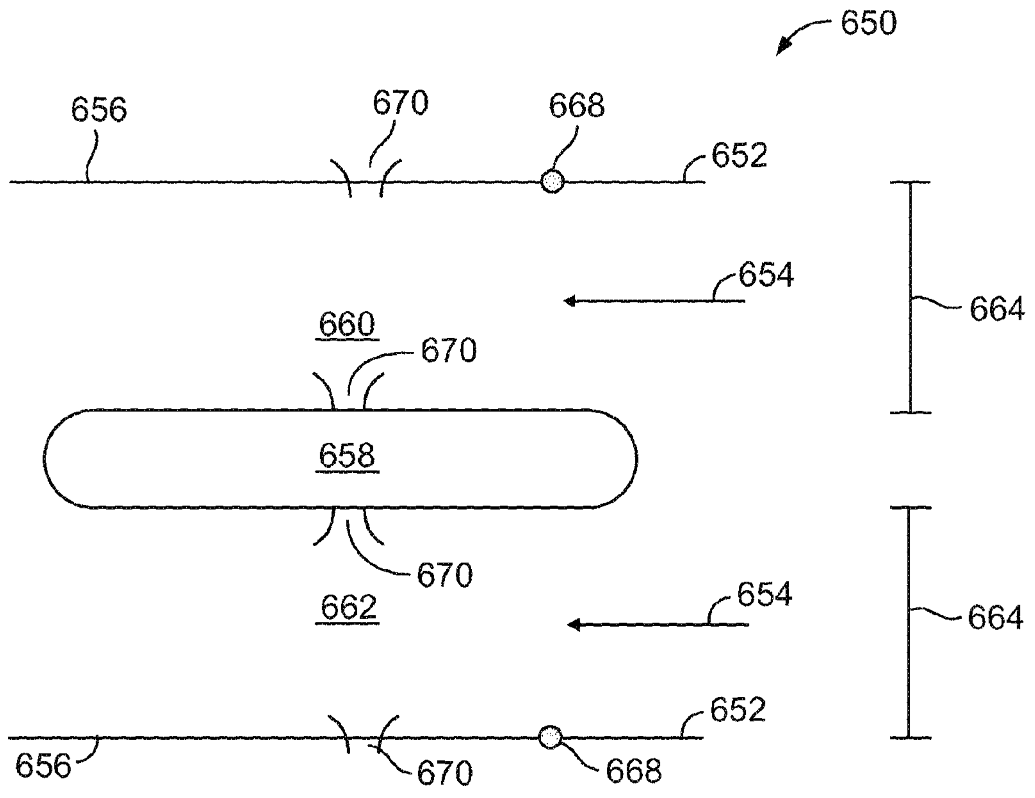
FIG. 10 is a schematic view of an active-passive sound attenuator in accordance with an embodiment.

FIG. 10 illustrates an active-passive sound attenuation system 650 in accordance with an embodiment. The system 650 is positioned within an air plenum 652 having airflow 654 therethrough. The plenum 652 includes a pair of walls 656. The walls 656 are arranged in parallel. Optionally, the walls 656 may be angled with respect to each other to provide a plenum width that converges and/or diverges. A sound-absorbing baffle 658 is positioned within the plenum 652. Air channels 660, 662 extend between the baffle 658 and the walls 656. In the exemplary embodiment, air channels 660, 662 have equivalent widths 664. Optionally, the baffle 658 may be positioned so that the widths 664 of channels 660 and 662 differ. The baffle 658 is also positioned in parallel with the walls 656. Optionally, the baffle 658 may be angled with respect to the walls 656. Additionally, the baffle 658 may be rounded and/or have any non-linear shape. The baffles 658 include a sound attenuating material. The sound attenuating material has a porous medium configured to absorb sound. For example, the sound attenuating material may include a fiberglass core.

A source microphone 668 is positioned within each wall 656. Optionally, the source microphone 668 may be positioned in only one wall 656. Alternatively, the source microphone 668 may be positioned within the baffle 658. The source microphone 668 may be positioned upstream from the baffle 658 or, optionally, downstream from the baffle 658. Speakers 670 are positioned within the walls 656. Alternatively, only one speaker 670 may be positioned within the wall. The speaker 670 may also be positioned within the baffle 658. The speaker 670 is positioned downstream from the source microphone 668. In one embodiment, the speaker 670 may be positioned downstream from the baffle 658 and configured to direct attenuating noise in a counter-direction of the airflow 654.

Additionally, speakers 670 may be positioned within or on the baffle 658. The speakers 670 may be aligned with, and oriented toward, the speakers 670 in the walls 656.

Noise generated within the plenum 652 travels upstream with airflow 654. The baffle 658 provides passive sound attenuation. Additionally, the source microphone 668 detects the noise to provide active sound attenuation. The speakers 670 transmit a sound attenuating noise which destructively interferes with the noise propagating through the plenum 652.

Figure 11:
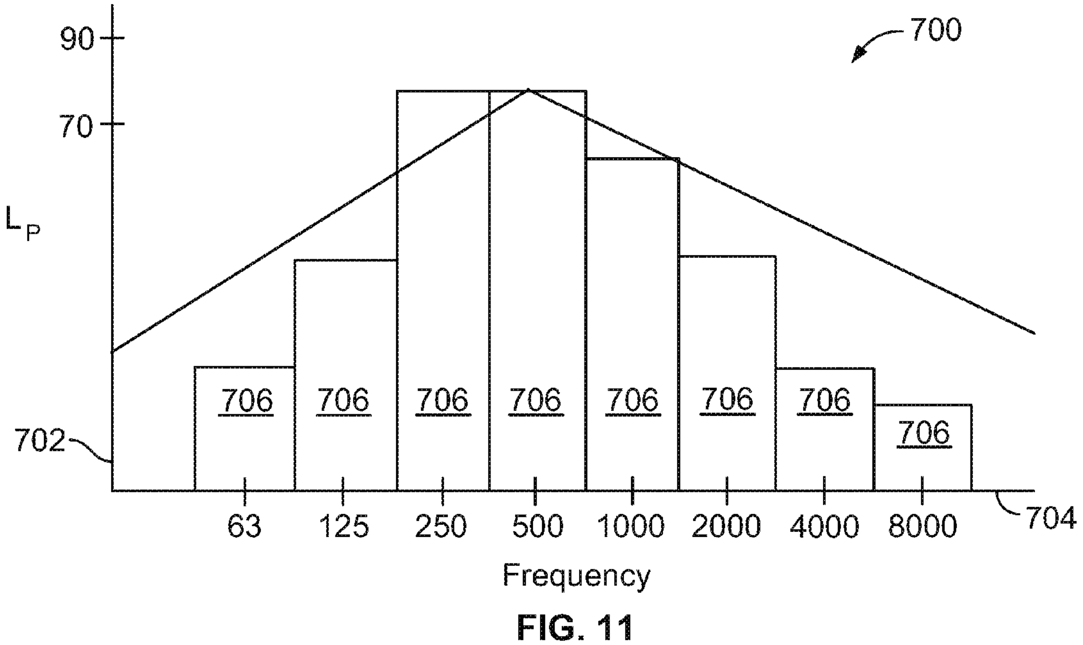
FIG. 11 is a chart illustrating noise frequencies attenuated in accordance with an embodiment.

FIG. 11 is a chart 700 illustrating a range of noise frequencies attenuated in accordance with an embodiment. The chart 700 includes sound pressure (Lp) on the y-axis 702 and frequency on the x-axis 704. Eight octave bands 706 are charted. Each octave band 706 includes a center frequency. The center frequencies illustrated are 63 Hz, 125 Hz, 250 Hz, 500 Hz, 1000 Hz, 2000 Hz, 4000 Hz, and 8000 Hz. The embodiments described herein are generally configured to attenuate noise generated in the octave bands 706. A dominant frequency component of fan noise may include the blade pass frequency. The blade pass frequency is determined using the following:

$$BPF=(RPM*\#\text{ of blades})/60$$

wherein BPF is the blade pass frequency, RPM is fan speed in revolutions per minute, and # of blades is the number of fan blades.

Figure 12:
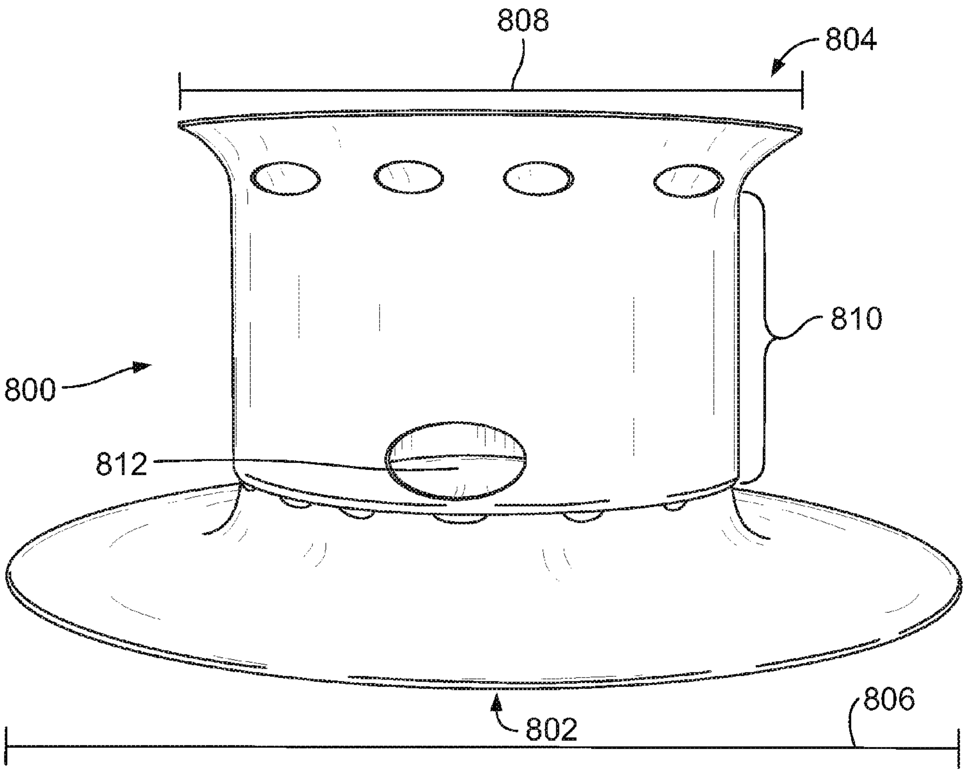
FIG. 12 is a side view of an inlet cone formed in accordance with an embodiment.

FIG. 12 is a side view of an inlet cone 800 formed in accordance with an embodiment. The inlet cone 800 includes an inlet 802 and an outlet 804. In an exemplary embodiment, the inlet 802 and the outlet 804 have a parabolic shape. In other embodiments, the inlet 802 and the outlet 804 may be various other shapes, such as shapes having multiple width radii. The inlet 802 has a width 806 that is greater than a width 808 of the outlet 804. The outlet 804 is configured to be positioned adjacent a fan wheel of a fan unit. In one embodiment, the outlet is coupled to the fan wheel. An intermediate portion 810 extends between the inlet 802 and the outlet 804. In the illustrated embodiment, the intermediate portion 810 is cylindrical in shape. In alternative embodiments, the intermediate portion 810 may have any suitable shape.

The intermediate portion 810 includes a plurality of apertures 812 formed therethrough. The apertures 812 are formed in an array around the intermediate portion. The apertures 812 are configured to retain speakers 814 (shown in FIG. 13) therein. The intermediate portion 810 may include any suitable number of apertures 812 for retaining any suitable number of speakers 814. The apertures 812 may be uniformly spaced about the intermediate portion 810. In one embodiment, the inlet cone 800 may includes apertures 812 in the inlet 802 and/or outlet 804.

Figure 13:
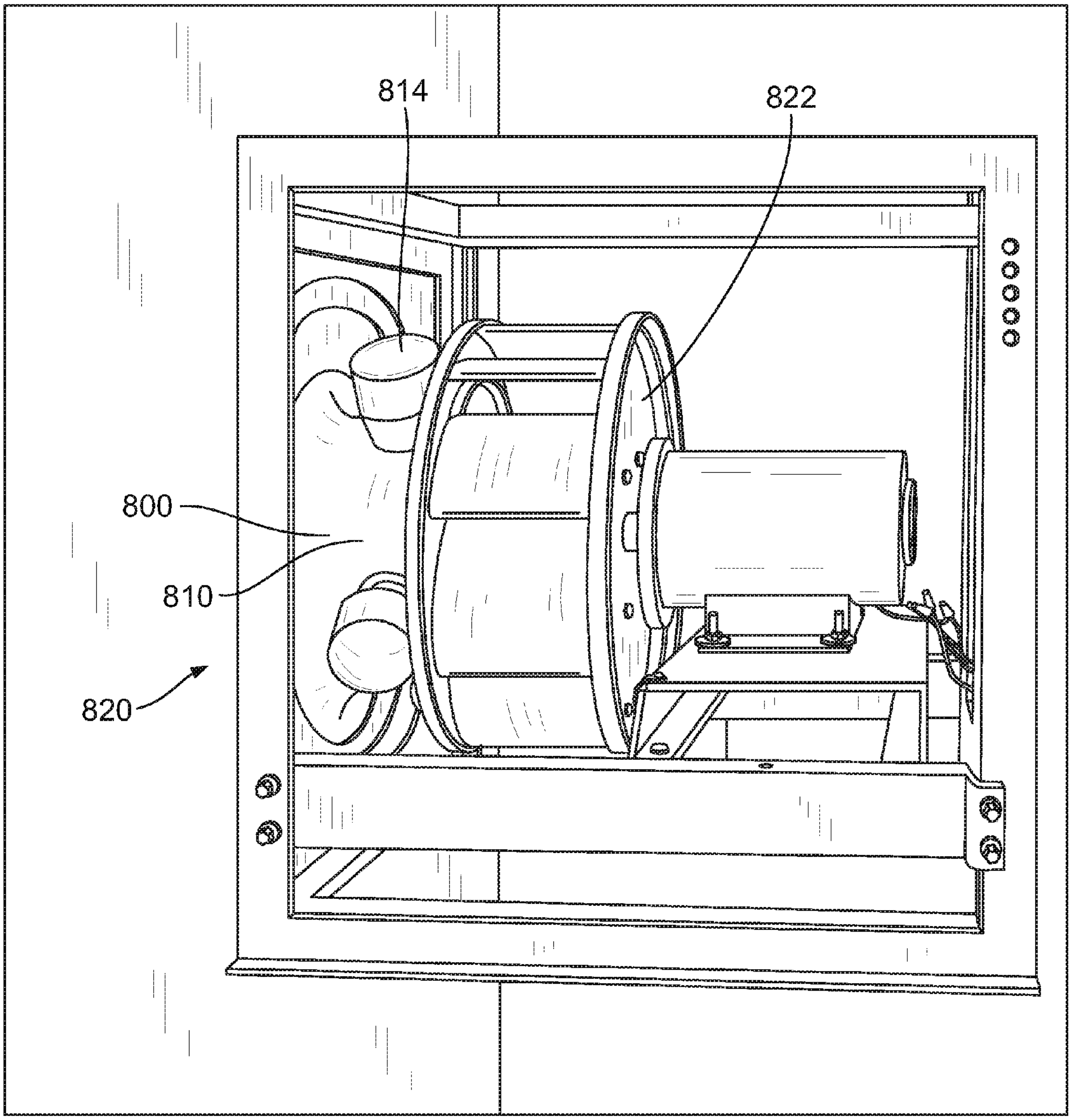
FIG. 13 is a side view of a fan unit formed in accordance with an embodiment.
Figure 14:
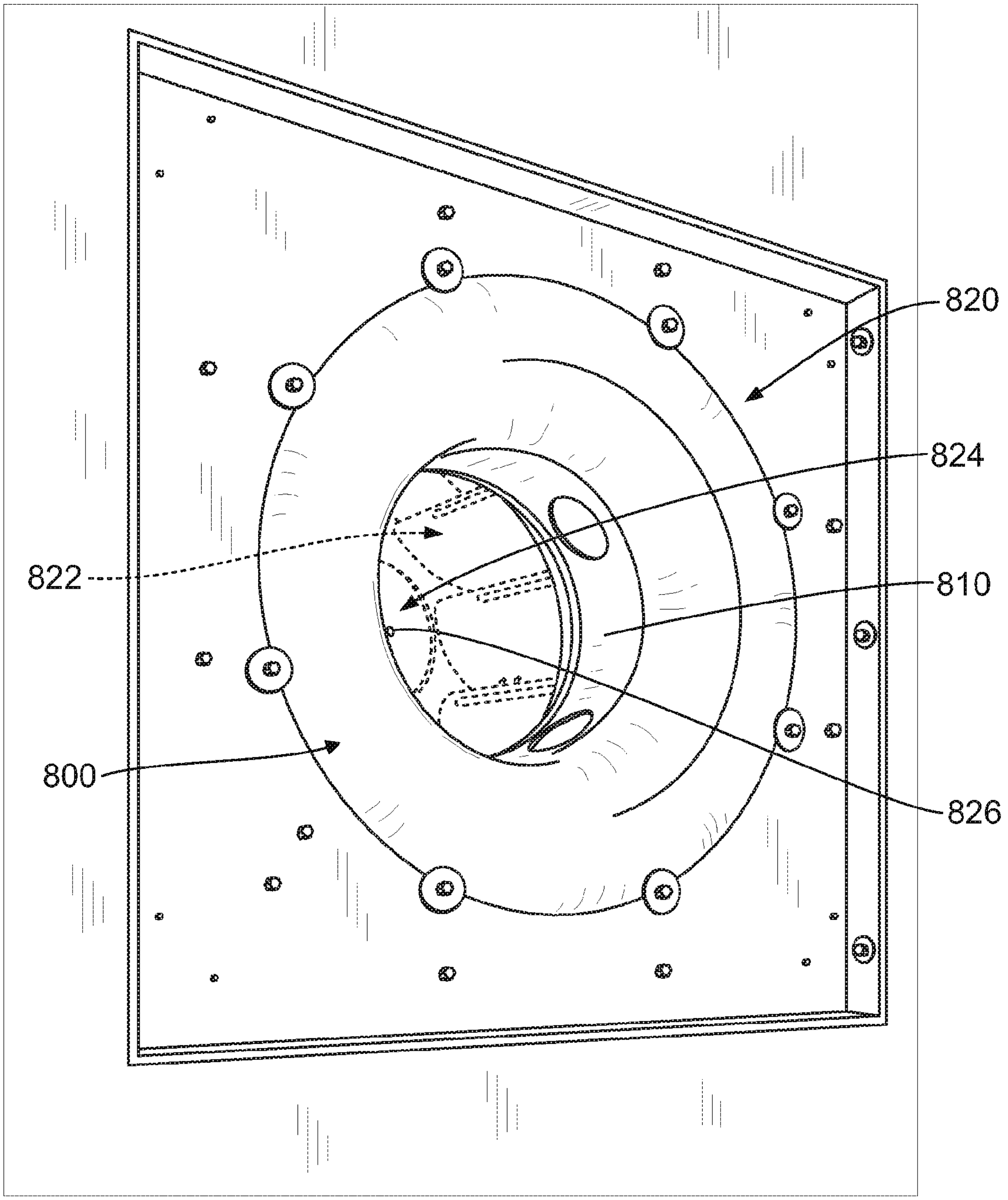
FIG. 14 is a front perspective view of a fan unit formed in accordance with an embodiment.

FIG. 13 is a side view of a fan unit 820 formed in accordance with an embodiment. FIG. 14 is a front perspective view of a fan unit 820. The fan unit 820 includes the inlet cone 800. The inlet cone 800 is joined to the fan wheel 822 of the fan unit 820. Speakers 814 are positioned in the apertures 812 (shown in FIG. 12) of the inlet cone 800. The speakers 814 are arranged in an array around the circumference of the inlet cone 800. The speakers 814 are arranged in an array around the circumference of the intermediate portion 810 of the inlet cone 800.

Figure 15:
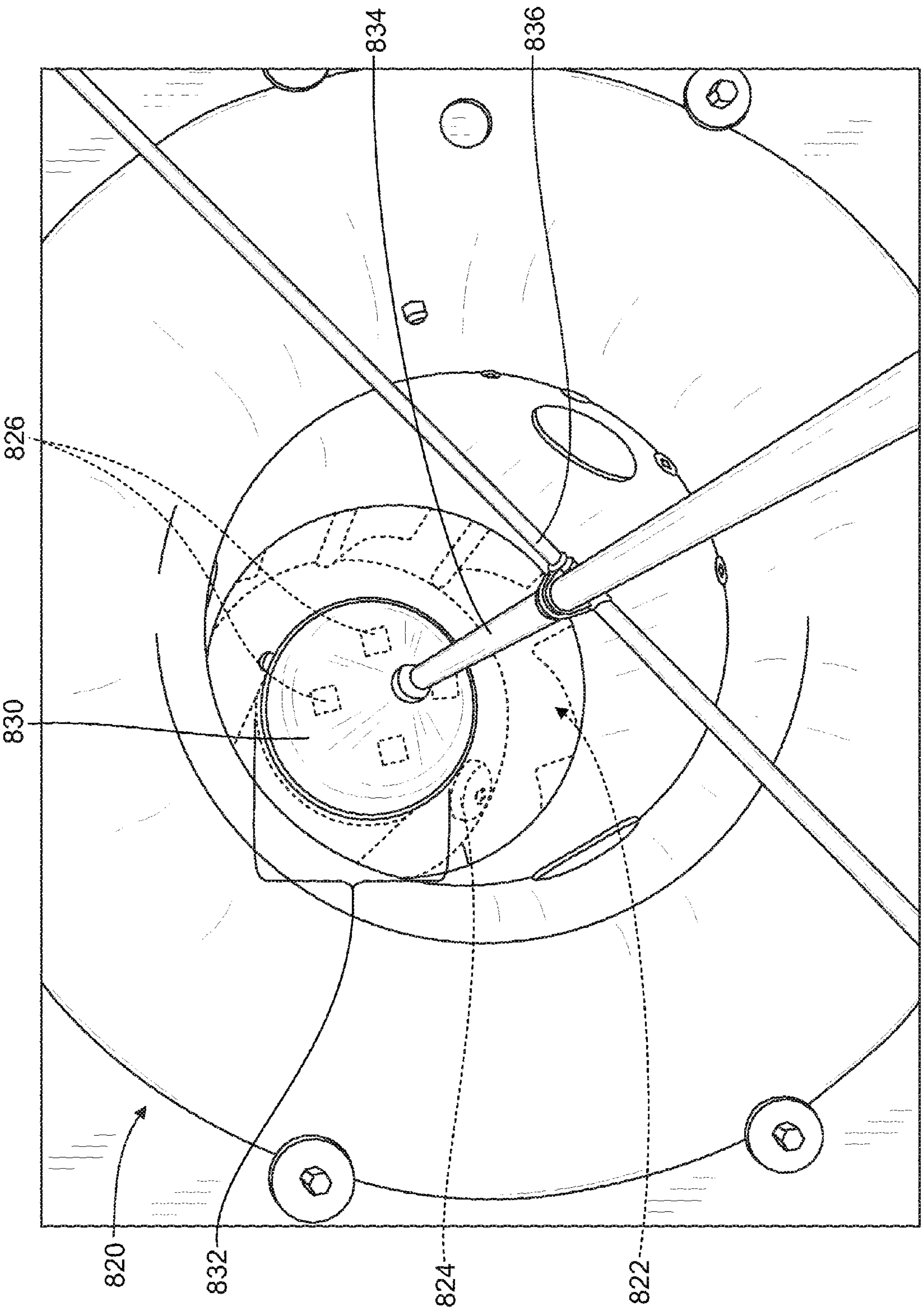
FIG. 15 is a front perspective view of the fan unit formed in accordance with an embodiment and having a microphone positioned therein.

FIG. 15 is a front perspective view of the fan unit 820 having a microphone 826 positioned therein. The fan wheel 822 includes a hub 824 having fan blades 828 extending therefrom. In an exemplary embodiment, a microphone assembly 832 is positioned with the hub 824 of the fan wheel 822. The microphone 826 is positioned within the microphone assembly 832. The illustrated embodiment includes four microphones 826 positioned in an array within the microphone assembly 832. In alternative embodiments, the fan unit 820 may include any number of microphones 826 arranged in any manner. For example, the fan unit 820 may include a single microphone 826 centered in the hub 824.

The microphone assembly 832 includes a cover 830 is positioned over the microphones 826. The cover 830 may be inserted into the hub 824 of the fan wheel 822. The cover 830 may abut the hub 824 of the fan wheel 822 in alternative embodiments. The cover 830 may be formed from a perforated material to allow sound waves to pass therethrough. The cover 830 may be formed from foam or the like in some embodiments. The cover 830 limits air flow to the microphones 826 while allowing sound waves to propagate to the microphones 826. The microphones 826 are configured to collect sound measurements from the fan unit 820. In response to the sound measurements, the array of speakers 814 generates a cancellation signal.

In the illustrated embodiment, the microphone assembly 832 is supported by a boom 834. The boom 834 retains the microphone assembly 832 within the hub 824 of the fan wheel 822. The boom 834 enables the fan wheel 822 to rotate with disturbing a position of the microphone assembly 832. The boom 834 is joined to a support beam 836 that retains a position of the boom 834 and the microphone assembly 832.

Figure 16:
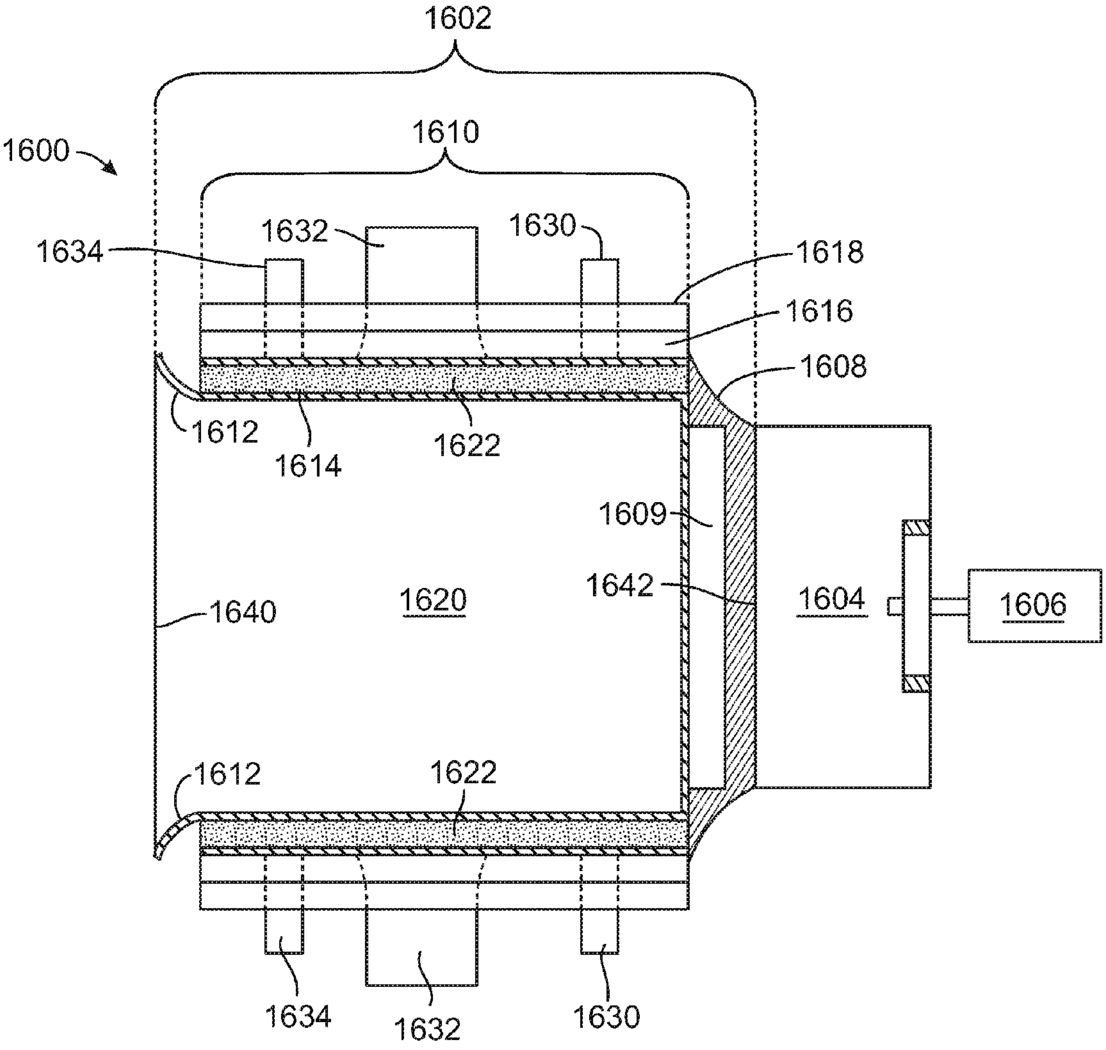
FIG. 16 illustrates a schematic view of a fan unit, according to an embodiment.

FIG. 16 illustrates a schematic view of a fan unit 1600, according to an embodiment. The fan unit 1600 includes an inlet cone 1602, a fan 1604, and a motor 1606. The inlet cone 1602 is positioned upstream from the fan 1604. The inlet cone 1602 includes a throat 1608 positioned directly upstream from the fan 1604. A metal tube 1609 may be disposed within the throat 1608. The metal tube 1609 may be a solid tube, for example. Optionally, the metal tube 1609 may be hollow. The metal tube 1609 may be used as a connection joint, and/or component configured to direct sound in a particular direction. It should be noted that with respect to airflow, "upstream" is defined as traveling from the fan 1604 to the inlet cone 1602 and "downstream" is defined as traveling from the inlet cone 1602 to the fan 1604.

The inlet cone 1602 also includes a noise control system or extension 1610 integrally connected between the throat 1608 and a distal inlet 1612. The noise control extension 1610 extends between the throat 1608 and the distal inlet 1612. The noise control extension 1610 may include a generally cylindrical tube 1614, which may be formed of perforated metal, plastic, or the like. A sound-absorbing layer 1616 is wrapped around the perforated tube 1614. A support cylinder 1618 may be wrapped around the sound-absorbing layer 1616.

The perforated tube 1614 is configured to allow sound to pass from an internal channel 1620 of the noise control extension 1610 into the sound-absorbing layer 1616. The perforated tube 1614 includes multiple perforations 1622 that allow sound energy to pass through the tube 1614 and into the sound-absorbing layer 1616. The perforated tube 1614 provides structural support for the sound-absorbing layer 1614, while, at the same time, allowing sound energy to pass into the sound-absorbing layer 1614 through the perforations 1622. Alternatively, the noise control extension 1610 may not include the perforated tube 1614. In this embodiment, the throat 1608 and the distal inlet 1612 connect directly to the sound-absorbing layer 1616. Further, the sound-absorbing layer 1616 may be formed of a relatively strong material that maintains its shape. Optionally, the sound-absorbing layer 1616 may include a rigid support layer connected to interior or outer walls thereof.

The sound-absorbing layer 1616 may be formed of a sound-absorbing material, such as melamine, fiberglass, open-cell foam, or even a closed-cell sound-absorbing material. In short, the sound-absorbing material may be formed of any material that is configured to absorb sound energy. The sound-absorbing layer 1616 may be approximately 3" thick. However, the sound-absorbing layer 1616 may be thicker or thinner than 3", depending on the desired level of sound-absorption.

The support cylinder 1618 wraps around the sound-absorbing layer 1616. The support cylinder 1618 may be formed of metal or plastic, and is configured to contain the sound-absorbing layer 1616. That is, the sound-absorbing layer 1616 may be compressively sandwiched between the support cylinder 1618 and the perforated tube 1614. Alternatively, the noise control extension 1610 may not include the support cylinder 1618.

The noise control extension 1610 may extend over a length of the inlet cone 1602 between the throat 1608 and the distal inlet 1612. The noise control extension 1610 may be approximately 18". Alternatively, the noise control extension 1610 may be longer or shorter than 18". However, it has been found that a noise control extension 1610 of approximately 12-18" provides significant sound attenuation.

In operation, the noise control extension 1610 provides passive attenuation for the fan unit 1600. The noise control extension 1610 also provides a suitable environment and/or support platform for active noise cancellation, as described above. Sound energy within the internal channel 1620 passes into the sound-absorbing layer 1616 through the perforations 1622 formed through the perforated tube 1614. The sound-absorbing layer 1616 absorbs the sound energy, thereby reducing the noise generated by the fan unit 1600.

Additionally, the noise control extension 1610 is configured to provide active noise attenuation, as described above. To that end, the noise control extension 1610 may also include one or more source or input microphones 1630 positioned proximate the throat 1608 of the inlet cone 1602. The source microphone(s) 1630 may include pairs of microphones. Optionally, the source microphone(s) 1630 may include only one microphone. The source microphone(s) 1630 may be mounted on the support cylinder 1618. Optionally, the source microphone(s) 1630 may extend through one or more of the support cylinder 1618, the sound-absorbing layer 1616, and the perforated tube 1614. The source microphone(s) 1630 may be configured and operate in a similar fashion to the source microphones described above.

A pair of speakers 1632 may be positioned upstream from the source microphone(s) 1630. Optionally, there may be additional speakers 1632. The speakers 1632 may be mounted on the support cylinder 1618, or may optionally extend through one or more of the support cylinder 1618, the sound-absorbing layer 1616, and the perforated tube 1614. The speakers 1632 may be aerodynamically configured to limit an effect on the fan performance. In an embodiment, the speakers 1632 may be positioned within the same cross-sectional plane. Optionally, the speakers 1632 may be offset from one another. The speakers 1632 may be configured and operate in a similar fashion to the speakers described above.

One or more response or error microphones 1634 may be positioned upstream of the speakers 1632. The response microphone(s) 1634 may be positioned within the inlet cone 1602. Optionally, the response microphone(s) 1634 may be positioned upstream of the fan unit 1600.

Noise generated by the fan 1604 travels upstream. The noise is detected by the source microphone(s) 1630. In response to the detected noise, the speakers 1632 transmit attenuating sound fields configured to destructively interfere with the noise. The result of the destructive interference is detected by the response microphone(s) 1634 to provide a feedback loop to the speakers 1632.

Noise generated by the fan 1604 may be generated by the interaction of the fan blade with the entering air stream. The entering air stream may not be completely laminar. As such, the entering air stream may have slight variations in a velocity profile and fan noise level. The non linearity of the entering stream may be caused by a velocity gradient at the face of the fan 1604, which, coupled with inlet swirl, may result in a fluctuating sound level. The fan 1604 may emit a sound profile that includes a combination of planar waves and non-planar waves. Non-planar waves are also known as cross modes. The volume of space within the extension 1610 may provide a region where the active attenuation devices may operate on a plane wave to enable active noise attenuation at the plane of the loudspeaker 1632. The out-of-phase signal generated by the active noise system may act primarily on waves.

Figure 17:
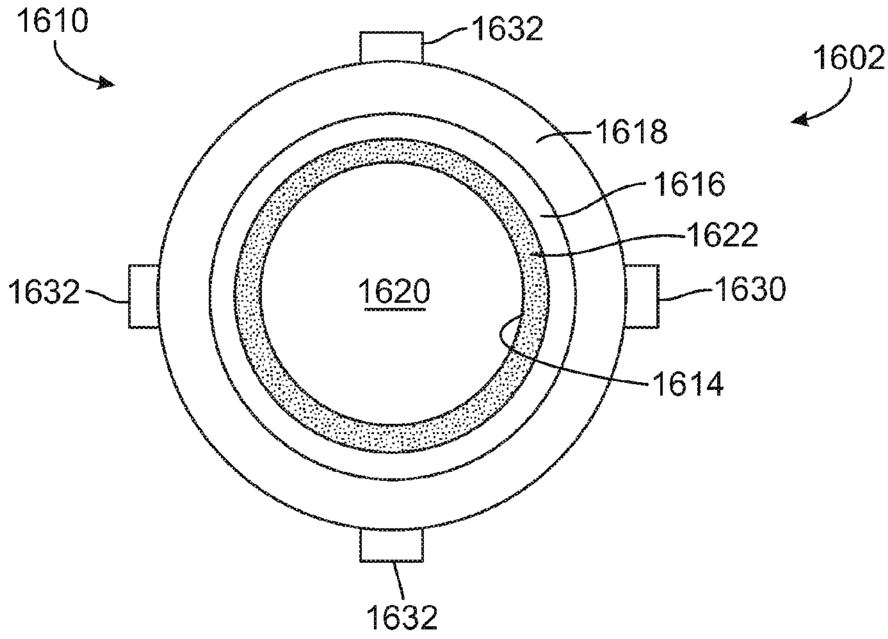
FIG. 17 illustrates a cross-sectional view of a noise control extension of an inlet cone, according to an embodiment.

FIG. 17 illustrates a cross-sectional view of the noise control extension 1610 of an inlet cone 1602, according to an embodiment. The inlet cone 1602 includes a source microphone 1630 and speakers 1632. The source microphone 1630 and the speakers 1632 are each positioned 90 degrees from each other. Optionally, the source microphone 1630 and the speakers 1632 may be positioned along any portion of the noise control extension 1610. Additionally, the inlet cone 1602 may include a pair of source microphones 1630 and/or any number of speakers 1632. In the example embodiment, the source microphone 1630 and the speakers 1632 may be positioned in the same cross-sectional plane of the noise control extension 1610. Optionally, the source microphone 1630 and the speakers 1632 may be offset from one another.

Noise travels through the inlet cone 1602. The noise is detected by the source microphone 1630. The speakers 1632 then generate an attenuation sound field to destructively interfere with the noise.

Referring to FIGS. 16 and 17, the noise control extension 1610 provides both passive and active sound attenuation. The noise control extension 1610 provides passive sound attenuation through the sound-absorbing layer 1616, for example, while also providing active sound attenuation through the microphones 1630 and 1634 and the speakers 1632, as described above.

The noise control system or extension 1610 may be directly mounted to the throat 1608 and the distal inlet 1640 of the inlet cone 1602. For example, the perforated tube 1614 and/or the support tube 1618 may be welded or otherwise permanently bonded to the throat 1608 and the distal inlet 1640. Optionally, the throat 1608, the tube 1614, and the distal inlet 1640 may be formed and molded as an integral piece. Alternatively, the noise control system or extension 1610 may simply abut against an existing inlet cone and secured thereto through adhesives, bonding, or the like. Existing fan units may be retrofit with the noise control system or extension 1610.

As shown in FIG. 16, the distal inlet 1612 has a diameter 1640 that is greater than the diameter 1642 of the throat 1608. However, the distal inlet 1612 and the throat 1608 may alternatively have diameters of similar length. Also, alternatively, the diameter of the throat 1608 may be larger than the diameter of the distal inlet 1640.

Additionally, the noise control extension 1610 is shown as a cylinder having a constant diameter throughout the length of the noise control extension 1610. However, the noise control extension 1610 may have a varying diameter over the length of the noise control extension 1610. For example, the diameter of the noise control extension 1610 proximate the throat 1608 may be smaller than the diameter of the noise control extension 1610 proximate the distal inlet 1640. The diameter of the noise control extension 1610 may gradually and constantly increase from the area proximate the throat 1608 to the area proximate the distal inlet 1640. Optionally, the diameter of the noise control extension may include stepped, abrupt changes from one end to the other.

Figure 18:
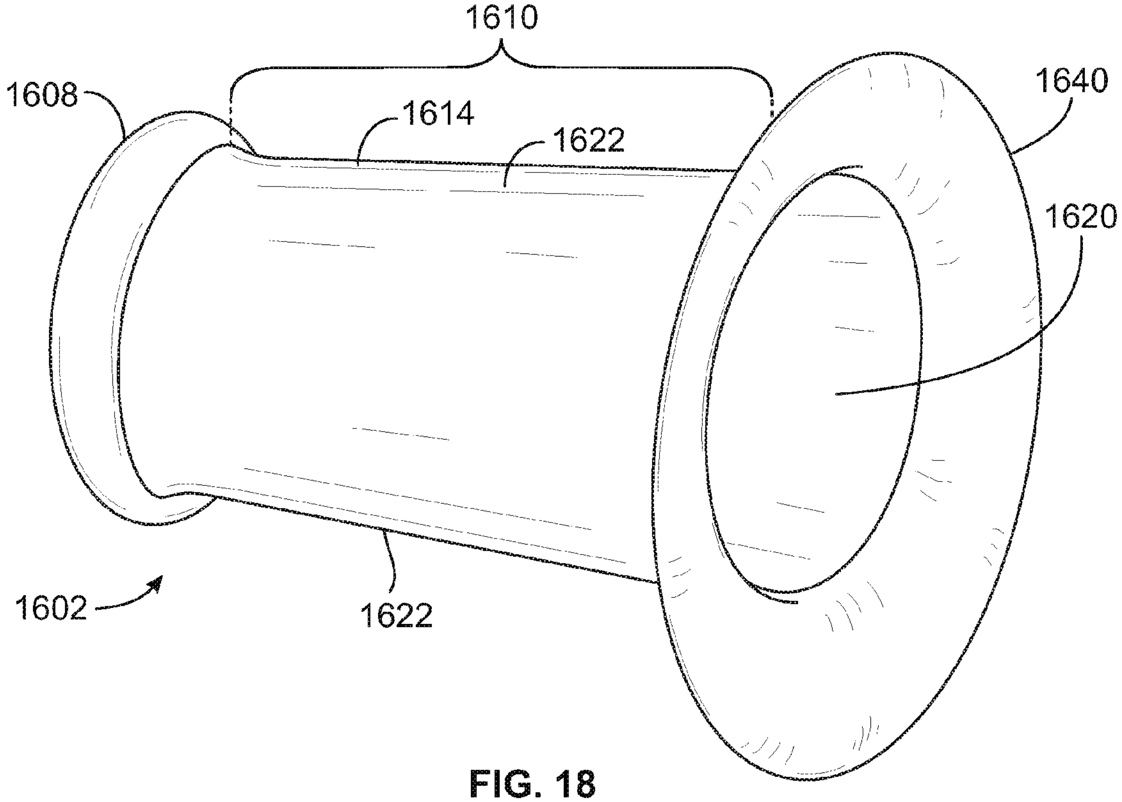
FIG. 18 illustrates a simplified isometric view of a perforated tube of a noise control extension of an inlet cone, according to an embodiment.

FIG. 18 illustrates a simplified isometric view of the perforated tube 1614 of the noise control extension 1610 of the inlet cone 1602, according to an embodiment. As shown in FIG. 18, the perforated tube 1614 may be a perforated metal cylinder that connects the throat 1608 to the distal inlet 1640.

Figure 19:
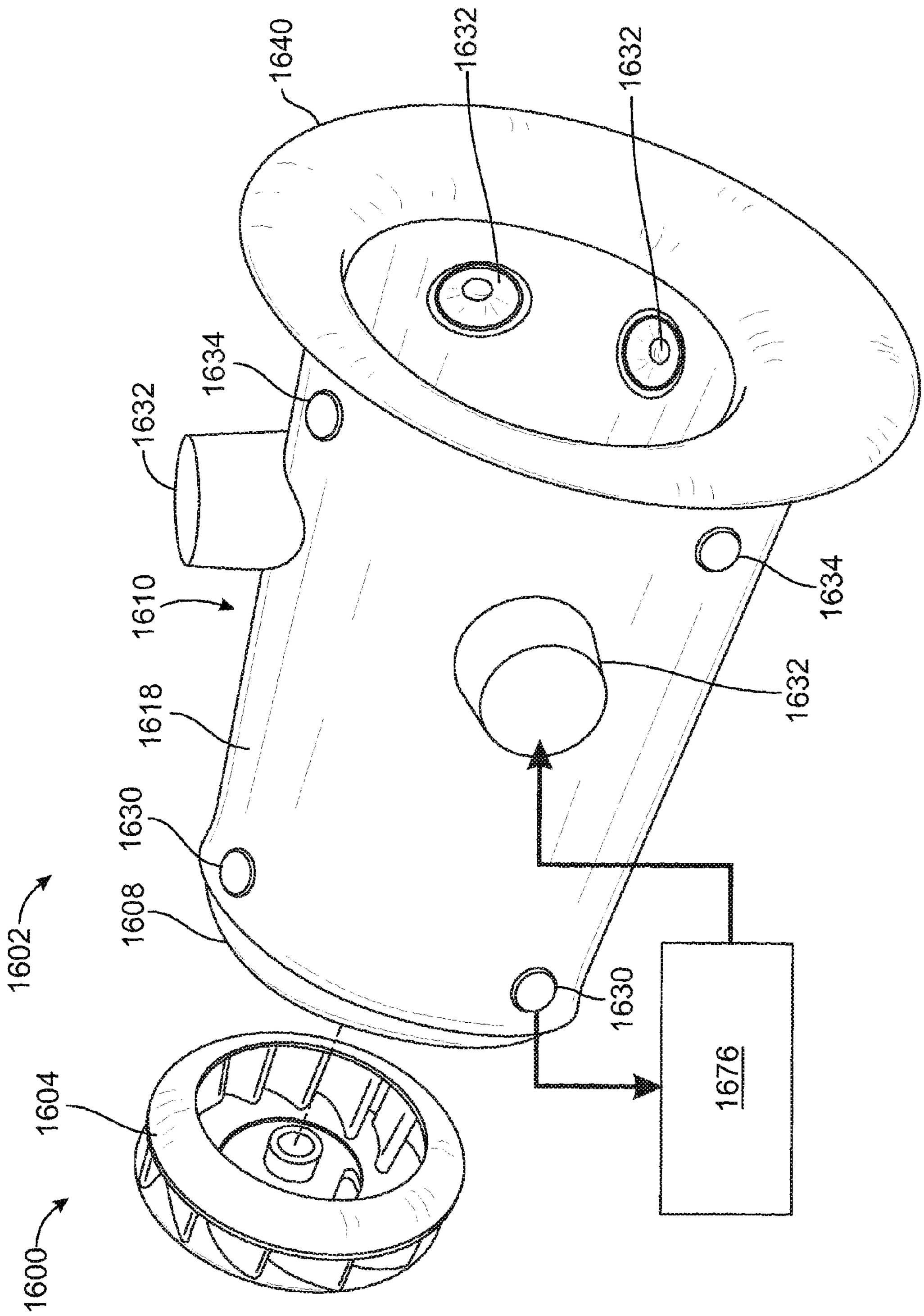
FIG. 19 illustrates a simplified isometric view of a fan unit, according to an embodiment.

FIG. 19 illustrates a simplified isometric view of the fan unit 1600, according to an embodiment. As described above, the fan unit 1600 may include the noise control extension 1610, which is configured to passively attenuate noise through the sound-absorbing layer 1616 (hidden from view of FIG. 19), and actively attenuate noise through the microphones 1630 and 1634 and the speakers 1632. The microphones 1630 and 1634 and the speakers 1632 are operatively connected to an attenuation module 1676, similar to the attenuation module 276 shown and described with respect to FIGS. 3 and 4. The attenuation module 1676 controls operation of the microphones 1630 and 1634 and the speakers 1632 as described above with respect to FIGS. 3 and 4.

Figure 20:
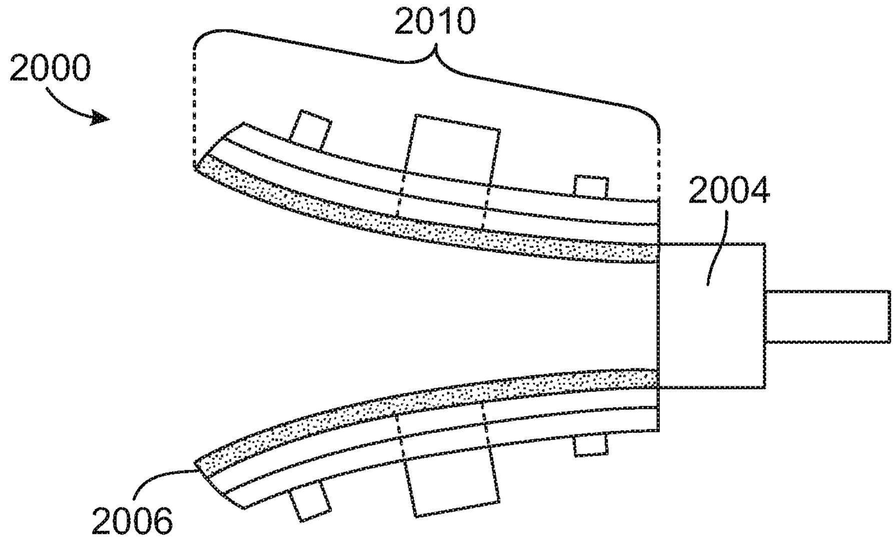
FIG. 20 illustrates a schematic view of a fan unit, according to an embodiment.

FIG. 20 illustrates a schematic view of a fan unit 2000, according to an embodiment. The fan unit 2000 is similar to the fan unit 1600 shown in FIG. 16, except that the noise control extension 2010 may be horn-shaped. That is, the diameter of the noise control extension 2010 may gradually and constantly increase from the fan 2004 toward a distal end 2006. The distal end 2006 of the noise control extension 2010 may flare outwardly. The diameter of the noise control extension 2010 may differ over a length of the noise control extension.

Figure 21:
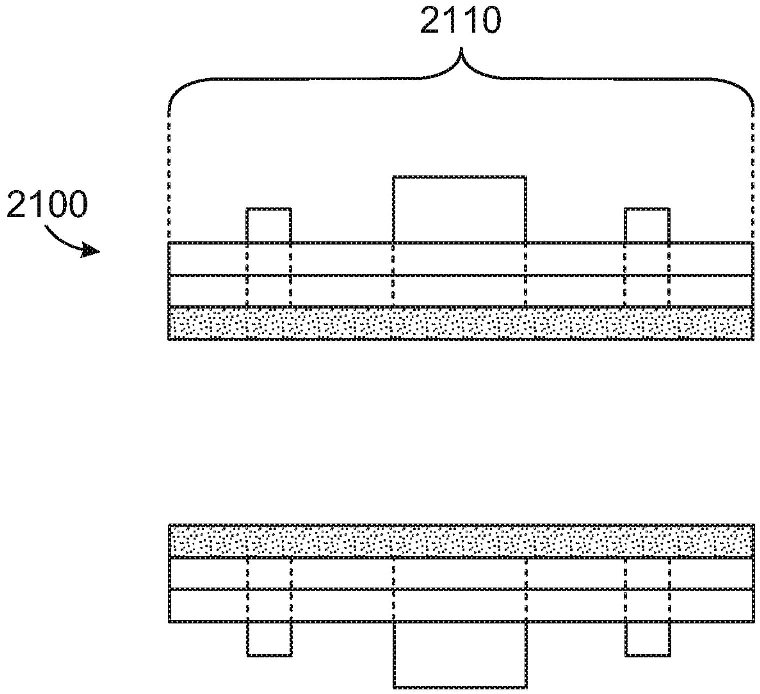
FIG. 21 illustrates a schematic view of a fan unit, according to an embodiment.

FIG. 21 illustrates a schematic view of a fan unit 2100, according to an embodiment. The fan unit 2010 is similar to the fan unit 1600 shown in FIG. 16, except that the noise control extension 2110 is simply a cylinder that does not connect to a throat or a distal end.

As noted above, the noise control extension may be various shapes and sizes, such as cylindrical, horn-shaped, cone-shaped, or the like. Additionally, the noise control extension may be of various lengths and diameters. While it has been found that 18" provides significant passive noise attenuation, the noise control extension may be various other lengths.

Referring to FIGS. 16-21, embodiments provide a system and method that enable fan units to operate at much lower noise levels, as compared to standard fans. Embodiments provide a noise control system that combines passive and active noise attenuation that reduces noise over a broad frequency range.

The embodiments described herein are described with respect to an air handling system. It should be noted that the embodiments described may be used within the air handling unit and/or in the inlet or discharge plenum of the air handling system. The embodiments may also be used upstream and/or downstream of the fan array within the air handling unit. Optionally, the described embodiments may be used in a clean room environment. The embodiments may be positioned in the discharged plenum and/or the return chase of the clean room. Optionally, the embodiments may be used in residential HVAC systems. The embodiments may be used in the ducts of an HVAC system. Optionally, the embodiments may be used with precision air control systems, DX and chilled-water air handlers, data center cooling systems, process cooling systems, humidification systems, and factory engineered unit controls. Optionally, the embodiments may be used with commercial and/or residential ventilation products. The embodiments may be used in the hood and/or inlet of the ventilation product. Optionally, the embodiments may be positioned downstream of the inlet in a duct and/or at a discharge vent.

The various embodiments described herein enable active monitoring of noise generated by a fan unit. By actively monitoring the noise, an attenuation signal is dynamically generated to cancel the noise. The attenuation signal is generated by inverting a noise signal acquired within the fan unit. Accordingly, attenuation is maximized by matching the amplitude of the noise signal. Additionally, the attenuation signal is configured to destructively interfere with the noise within a range defined inside the fan unit cone. As a result, the noise generated by the fan is attenuated prior to exiting the fan unit. The response microphone enables continual feedback of the attenuation, thereby promoting the dynamic changes of the system.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A fan unit, comprising:

a fan operatively connected to a motor; and an inlet cone proximate to the fan, wherein the inlet cone comprises:

a throat proximate the fan;

a distal inlet; and a noise control extension extending between the throat and the distal inlet, wherein the noise control extension has a sound-absorbing layer configured to passively attenuate sound generated by the fan unit.

2. The fan unit of claim 1, further comprising:

a source microphone configured to collect sound produced by the fan unit; and a speaker configured to generate a cancellation sound field that at least partially cancels the sound.

3. The fan unit of claim 1, wherein the noise control extension further comprises a perforated tube, wherein the sound-absorbing layer wraps around at least a portion of the perforated tube.

4. The fan unit of claim 1, wherein the noise control extension further comprises a support tube that wraps around at least a portion of the sound-absorbing layer.

5. The fan unit of claim 2, wherein the source microphone and the speaker are directly or indirectly secured to the support tube.

6. The fan unit of claim 1, wherein the sound-absorbing layer is formed of an open-cell sound-absorbing material.

7. The fan unit of claim 1, wherein the noise control extension is cylindrical.

8. The fan unit of claim 1, wherein the noise control extension comprises a diameter that differs throughout at least a portion of a length of the noise control extension.

9. The fan unit of claim 2, further comprising at least one response microphone configured to provide a feedback loop to the speaker.

10. The fan unit of claim 2, further comprising a module configured to define the cancellation signal that at least partially cancels out the sound measurements.

11. A fan unit, comprising:

a fan operatively connected to a motor;

an inlet cone proximate to the fan, wherein the inlet cone includes a noise control extension having a sound-absorbing layer configured to passively attenuate sound generated by the fan unit;

a source microphone configured to collect sound produced by the fan unit;

a speaker configured to generate a cancellation sound field that at least partially cancels the sound; and at least one response microphone configured to provide a feedback loop to the speaker.

12. A method of attenuating noise within a fan unit, wherein the fan unit comprises a fan operatively connected to a motor and an inlet cone proximate to the fan, the method comprising:

disposing a noise control extension having a sound-absorbing layer that is configured to passively attenuate sound generated by the fan between a throat and distal end of the inlet cone; and passively attenuating noise generated within the fan unit with the noise control extension.

13. The method of claim 12, further comprising actively attenuating noise generated within the fan unit, wherein the actively attenuating noise operation comprises collecting sound generated by the fan unit through a source microphone, and generating a cancellation sound field that at least partially cancels the sound through a speaker.

14. The method of claim 12, wherein the passively attenuating noise operation further comprises:

supporting the sound-absorbing layer with a perforated tube; and allowing sound to pass into the sound-absorbing layer through the perforated tube.

15. The method of claim 12, wherein the passively attenuating noise operation further comprises supporting the sound-absorbing layer with a support tube that wraps around at least a portion of the sound-absorbing layer.

16. The method of claim 13, further comprising securing the source microphone and the speaker to the support tube.

17. The method of claim 12, further comprising forming the sound-absorbing layer from an open-cell sound-absorbing material.

18. The method of claim 13, further comprising using at least one response microphone to provide a feedback loop to the speaker.

19. The method of claim 13, wherein the actively attenuating operation further comprises defining the cancellation signal with a module.

20. A method of attenuating noise within a fan unit, wherein the fan unit comprises a fan operatively connected to a motor and an inlet cone proximate to the fan, the method comprising:

passively attenuating noise generated within the fan unit with a noise control extension having a sound-absorbing layer configured to passively attenuate sound generated by the fan;

actively attenuating noise generated within the fan unit, wherein the actively attenuating noise operation comprises collecting sound generated by the fan unit through a source microphone, and generating a cancellation sound field that at least partially cancels the sound through a speaker; and using at least one response microphone to provide a feedback loop to the speaker.

21. A fan unit, comprising:

a noise control extension configured to extend between a throat and a distal inlet of an inlet cone, wherein the noise control extension has a sound-absorbing layer configured to passively attenuate sound generated by a fan unit;

a source microphone configured to collect sound produced by the fan unit; and a speaker configured to generate a cancellation sound field that at least partially cancels the sound.

22. The fan unit of claim 21, wherein the noise control extension further comprises a perforated tube, wherein the sound-absorbing layer wraps around at least a portion of the perforated tube.

23. The fan unit of claim 21, wherein the noise control extension further comprises a support tube that wraps around at least a portion of the sound-absorbing layer.

24. The fan unit of claim 23, wherein the source microphone and the speaker are directly or indirectly secured to the support tube.

25. The fan unit of claim 21, wherein the sound-absorbing layer is formed of an open-cell sound-absorbing material.

26. The fan unit of claim 21, wherein the noise control extension is cylindrical.

27. The fan unit of claim 21, wherein the noise control extension comprises a diameter that differs throughout at least a portion of a length of the noise control extension.

28. The fan unit of claim 21, further comprising at least one response microphone configured to provide a feedback loop to the speaker.

29. The fan unit of claim 21, further comprising a module configured to define the cancellation signal that at least partially cancels out the sound measurements.

30. A fan unit, comprising:

a noise control extension having a sound-absorbing layer configured to passively attenuate sound generated by a fan unit;

a source microphone configured to collect sound produced by the fan unit;

a speaker configured to generate a cancellation sound field that at least partially cancels the sound; and at least one response microphone configured to provide a feedback loop to the speaker.

* * * * *